United States Patent [19]

Morella et al.

[11] Patent Number: 5,378,474
[45] Date of Patent: * Jan. 3, 1995

[54] SUSTAINED RELEASE PHARMACEUTICAL COMPOSITION

[75] Inventors: Angelo M. Morella, Campbelltown; Mark C. Fisher, Birkenhead, both of Australia

[73] Assignee: F.H. Faulding & Co. Limited, Parkside, Australia

[*] Notice: The portion of the term of this patent subsequent to Mar. 23, 2010 has been disclaimed.

[21] Appl. No.: 21,276

[22] Filed: Feb. 22, 1993

Related U.S. Application Data

[63] Continuation of Ser. No. 574,551, Aug. 24, 1990, Pat. No. 5,202,128, which is a continuation-in-part of Ser. No. 461,370, Jan. 5, 1990, abandoned.

[30] Foreign Application Priority Data

Jan. 6, 1989 [AU] Australia .................... PJ2192

[51] Int. Cl.⁶ .................... A61K 9/24; A61K 9/58
[52] U.S. Cl. .................... 424/469; 424/461; 424/462; 424/468; 424/489; 424/490; 424/493; 424/494; 424/495; 424/497
[58] Field of Search ............... 424/497, 461, 462, 490, 424/617, 682, 468, 493–495, 469

[56] References Cited

U.S. PATENT DOCUMENTS

| | | | |
|---|---|---|---|
| 4,708,874 | 11/1987 | Haan et al. | 424/470 |
| 4,713,248 | 12/1987 | Kjorn et al. | 424/468 |
| 4,800,087 | 1/1989 | Mehta | 424/497 |
| 4,851,228 | 7/1989 | Zentner et al. | 424/456 |
| 5,196,203 | 3/1993 | Boehm | 424/469 |
| 5,202,128 | 4/1993 | Morella | 424/469 |

FOREIGN PATENT DOCUMENTS 43236 12/1985 Australia .

*Primary Examiner*—G. S. Kishore
*Attorney, Agent, or Firm*—Darby & Darby

[57] ABSTRACT

The present invention relates to a pharmaceutical pellet composition having a core element including at least one highly soluble active ingredient and a core coating which is partially soluble at a highly acidic pH. The pharmaceutical composition provides a slow release of active ingredient at a highly acidic pH and provides a constant, relatively faster rate of release at a more alkaline pH such as that of the intestine. Oral administration of the pharmaceutical pellet composition of the present invention to a patient is effective to deliver to the blood levels of active ingredient within the therapeutic range and to maintain such levels over an extended period of time.

21 Claims, 6 Drawing Sheets

SUSTAINED RELEASE PHARMACEUTICAL COMPOSITION

This is a continuation of application Ser. No. 07/574,551, filed Aug. 24, 1990, now U.S. Pat. No. 5,202,128 which, in turn, is a continuation-in-part of application Ser. No. 07/461,370, filed Jan. 5, 1990, now abandoned.

The present invention relates to a sustained release pharmaceutical composition, in particular a sustained release pharmaceutical composition including an active ingredient of high solubility in water, and to a method of preparing same.

As is known in the prior art, it is desirable in the treatment of a number of diseases, both therapeutically and prophylactically to provide the active pharmaceutical ingredient in a sustained release form. Desirably the sustained release provides a generally constant rate of release over an extended period. Whilst there is known in the prior art numerous sustained release formulations, the extension of sustained release regimens to active pharmaceutical ingredients of high solubility in water has been extremely limited. It has been found in the prior art that the high solubility in water of the active ingredient tends to generate a product which is susceptible to the phenomenon known as "dose dumping". That is, release of the active ingredient is delayed for a time but once release begins the rate of release is very high. Moreover, fluctuations tend to occur in the plasma concentrations of active ingredient which increases the likelihood of toxicity. Further, some degree of diurnal variation in plasma concentration of active ingredient has also been noted.

Prior art preparations may also suffer from other disadvantages, for example bioavailability of prior art preparations may be compromised by food. This is important since complex dosage regimens may lead to non-compliance.

For example, typical highly water soluble active ingredients include the opioid drugs which still play a major role in the treatment of acute and chronic pain, particularly pain associated with terminal diseases such as cancer.

Morphine is regarded as the opioid drug of choice in the treatment of cancer pain. It is universally acknowledged that the oral route of administration is preferred if sufficient pain relief can be obtained with an acceptable profile of side effects with respect to incidence and severity. Until recently, the liquid or immediate release tablet formulations of morphine were the only dosage forms available physicians for oral administration in the treatment of cancer pain.

The oral administration of morphine has had many critics in the prior art who point to a supposed lack of efficacy. However, the accumulated evidence, particularly from the hospice environment, indicates that this criticism is unfounded if the dose and dosing interval are specifically optimized for each patient, the morphine doses are administered before the pain returns and in a strictly regular regimen. In practical terms, this means morphine doses ranging from 10 mg to in excess of 500 mg with dosing intervals ranging from every 2 to 6 hours. A relationship between blood morphine concentration and pain relief has been established in the treatment of post-operative and cancer pain.

The studies propose that there is a minimum effective concentration (MEC) for morphine for each patient. There is a five-fold interpatient variation in MEC in the treatment of post-operative pain and an even greater variation for cancer pain. This concept of a MEC for opioids has also been demonstrated for pethidine, methadone, fentanyl and ketobemidone. Repeated oral or parenteral doses produce fluctuating blood opioid concentrations, with the peak concentrations sometimes resulting in side effects, while the trough concentrations are usually associated with inadequate pain relief. Therefore, a formulation of morphine which reduces the fluctuations in blood opioid concentrations and has a longer duration of pain relief (e.g. a. sustained release preparation) has widespread potential to improve pain relief in terminal care.

Currently, there is only one such preparation (MST Continus or MS Contin) being marketed world-wide. However, the combined pharmacokinetic and pharmacodynamic data suggest that this product is actually a delayed release formulation with some sustained release characteristics. While the manufacturers recommend a 12 hour dosing interval, extensive clinical experience suggests that an 8 hour interval is more realistic for continuous pain control.

Accordingly, it is an object of the present invention to overcome, or at least alleviate, one or more of the difficulties related to the prior art.

Accordingly, it is a first aspect of the present invention there is provided a sustained release pharmaceutical pellet composition including
- a core element including at least one active ingredient of high solubility; and
- a core coating for the core element which is partially soluble at a highly acidic pH to provide a slow rate of release of active ingredient and wherein the active ingredient is available for absorption at a relatively constant faster rate in the intestine over an extended period of time, such that blood levels of active ingredient are maintained within the therapeutic range over an extended period of time.

By "sustained release" as used herein we mean release of active ingredient at such a rate that blood levels are maintained within the therapeutic range but below toxic levels over an extended period of time e.g. 10 to 24 hours or greater. By "active ingredient of high water solubility" as used herein we mean pharmaceutically active, orally acceptable ingredients having an aqueous solubility of approximately 1 in 30 or above.

By "bioavailability" as used herein we mean the extent to which the active drug ingredient is absorbed from the drug product and becomes available at the site of drug action.

BRIEF DESCRIPTIONS OF THE DRAWINGS

Figure 1:
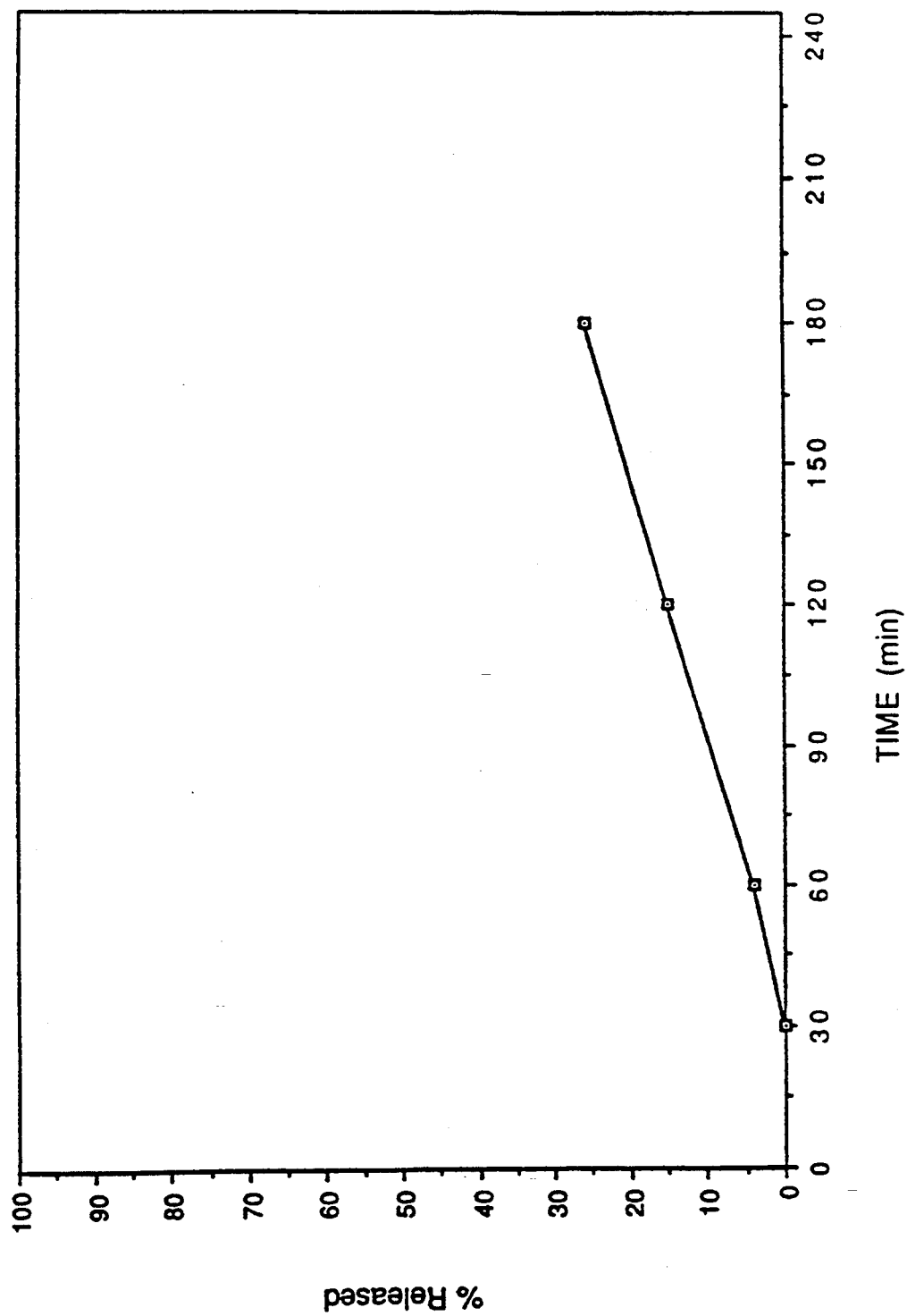
FIG. 1 shows the dissolution profile of morphine sulfate Formulation 1 at pH 1.2.

The active ingredients of high solubility may be selected from the group consisting of antihistamines, antiobiotics, antituberculosis agents, colinergic agents, antimuscarinics, sympathomimetics, sympatholytic agents, autonomic drugs, iron preparations, haemostatics, cardiac drugs, antihypertensive agents, vasodilators, non-steroidal antiinflammatory agents, opiate agonists, anticonvulsants, tranquilizers, stimulants, barbiturates, sedatives, expectorants, antiemetics, gastrointestinal drugs, heavy metal antagonists, antithyroid agents, genitourinary smooth muscle relaxants and vitamins. The invention is applicable to active ingredients of high solubility whether the solubility characteristics are pH dependent or pH independent.

Examples of active ingredients of high solubility are set out in the table below. The listed solubilities are in 1 part soluble in so many parts water.

| DRUG | SOLUBILITY (AQUEOUS) | pKA |
|---|---|---|
| Antihistamines | | |
| Azatadine maleate | very soluble | 9.3 |
| Brompheniramine maleate | 1 in 5 | 3.59, 9.12 |
| Carbinoxamine maleate | 1 in 1 | 8.1 |
| Chlorpheniramine maleate | 1 in 4 | 9.2 |
| Dexchlorpheniramine maleate | 1 in 1.1 | |
| Diphenhydramine HCl | 1 in 1 | 9.0 |
| Doxylamine succinate | 1 in 1 | 5.8, 9.3 |
| Methdilazine HCl | 1 in 2 | 7.5 |
| Promethazine | 1 in 0.6 | 9.1 |
| Trimeprazine Tartrate | 1 in 4 | |
| Tripelennamine citrate | 1 in 1 | 3.9, 9.0 |
| Tripelennamine HCl | 1 in 1 | |
| Triprolidine HCl | 1 in 2 | 3.6, 9.0 |
| Antibiotics | | |
| Penicillin V Potassium | 1 in 1.5 | 0.5 |
| Cloxacillin sodium | 1 in 2.5 | 2.7 |
| Dicloxacillin sodium | freely soluble | 2.7 |
| Nafcillin Sodium | freely soluble | 2.7 |
| Oxacillin Sodium | 1 in 3.5 | 2.8 |
| Carbenicillin Indanyl Sodium | freely soluble | 2.6, 2.7, 3.3 |
| Oxytetracycline HCl | 1 in 2 | 3.31 7.3, 9.1 |
| Tetracycline HCl | 1 in 10 | 3.3, 7.7, 9.7 |
| Clindamycin Phosphate | 1 in 2.5 | 7.7 |
| Clindamycin HCl | 1 in 2 | 7.7 |
| Clindamycin Palmitate HCl | freely soluble | |
| Lincomycin HCl | 1 in 1 | 7.6 |
| Novobiocin Sodium | 1 in 5 | 4.2, 9.1 |
| Nitrofurantoin Sodium | soluble | 7.2 |
| Metronidazole hydrochloride | 1 in 1 | 2.6 |
| Antituberculosis Agents | | |
| Isoniazid | 1 in 8 | 1.8, 3.5, 10.8 |
| Cholinergic Agents | | |
| Ambenonium chloride | 1 in 5 | |
| Bethanecol chloride | 1 in 1 | |
| Neostigmine bromide | 1 in 0.5 | 12.0 |
| Pyridostigmine bromide | 1 in 1 | |
| Antimuscarinics | | |
| Anisotropine methylbromide | soluble | |
| Clidinium bromide | soluble | |
| Dicyclomine HCl | 1 in 20 | 9 |
| Glycopyrrolate | 1 in 5 | |
| Hexocyclium methylsulfate | freely soluble | |
| Homatropine methylbromide | 1 in 6 | 9.9 |
| Hyoscyamine sulphate | 2 in 1 | 3.5 |
| Methantheline bromide | 1 in 5 | |
| Hyoscine hydrobromide | 1 in 3 | 7.6 |
| Oxyphenonium bromide | freely soluble | 3.2 |
| Propantheline bromide | very soluble | 9.0 |
| Tridihexethyl chloride | 1 in 3 | |
| Sympathomimetics | | |
| Bitolterol Mesylate | | 9.1 |
| Ephedrine | 1 in 20 | 9.6 |
| Ephedrine HCl | 1 in 3 | 9.6 |
| Ephedrine sulphate | 1 in 1 | 9.6 |
| Orciprenaline sulphate | 1 in 2 | 9.0, 10.1, 11.4 |
| Phenylpropanolamine hydrochloride | 1 in 2.5 | 9 |
| Pseudoephedrine hydrochloride | 1 in 1 | 9.8 |
| Ritodrine hydrochloride | 1 in 10 | 9 |

-continued

| DRUG | SOLUBILITY (AQUEOUS) | pKA |
|---|---|---|
| Salbutamol sulphate | 1 in 4 | 9.3, 10.3 |
| Terbutaline sulphate | 1 in 4 | 8.7, 10.0, 11.0 |
| Symnatholytic Agents | | |
| Phenoxybenzamine hydrochloride | 1 in 25 | 4.4 |
| Miscellaneous Autonomic Drugs | | |
| Nicotine | soluble | 7.9 |
| Iron Preparations | | |
| Ferrous gluconate | 1 in 10 | |
| Ferrous sulphate | 1 in 5 | |
| Haemostatics | | |
| Aminocaproic acid | 1 in 1.5 | 4.43, 10.73 |
| Cardiac Drugs | | |
| Acebutolol HCl | 1 in 5 | 9.4 |
| Diltiazem hydrochloride | freely soluble | 7.7 |
| Disopyramide phosphate | 1 in 20 | 8.4 |
| Flecainide acetate | 1 in 20 | 9.3 |
| Procainamide hydrochloride | 1 in 0.25 | 9.23 |
| Propranolol hydrochloride | 1 in 20 | 9.5 |
| Quinidine Gluconate | freely soluble | 4.0, 8.6 |
| Timolol maleate | freely soluble | 9 |
| Tocainide hydrochloride | freely soluble | 7.8 |
| Verapamil hydrochloride | 1 in 20 | 4–6.5 |
| Antihypertensive Agents | | |
| Captopril | freely soluble | 3.7, 9.8 |
| Clonidine hydrochloride | 1 in 13 | 8.2 |
| Hydralazine hydrochloride | 1 in 25 | 7.3 |
| Mecamylamine hydrochloride | 1 in 5 | 11.2 |
| Metoprolol tartrate | very soluble | 9.68 |
| Vasodilators | | |
| Papaverine hydrochloride | 1 in 2 | 6.4 |
| Non-Steroidal Antiinflammatory Agents | | |
| Choline salicylate | very soluble | |
| Magnesium salicylate | 1 in 13 | |
| Meclofenamate sodium | freely soluble | 4.0 |
| Naproxen sodium | soluble | 4.15 |
| Tolmetin sodium | freely soluble | 3.5 |
| Opiate Agonists | | |
| Codeine HCl | 1 in 30 | 8.2 |
| Codeine phosphate | 1 in 4 | 8.2 |
| Codeine sulphate | 1 in 30 | 8.2 |
| Dextromoramide tartrate | 1 in 25 | 7.1 |
| Hydrocodone bitartrate | 1 in 10 | 8.3 |
| Hydromorphone hydrochloride | 1 in 3 | 8.2 |
| Pethidine hydrochloride | very soluble | 8.7 |
| Methadone hydrochloride | 1 in 2 | 8.3 |
| Morphine sulphate | 1 in 15.5 | 8.0, 9.9 |
| Morphine acetate | 1 in 2.25 | |
| Morphine lactate | 1 in 10 | |
| Morphine meconate | 1 in 20 | |
| Morphine nitrate | 1 in 1.5 | |
| Morphine monobasic phosphate | 1 in 5 | |
| Morphine tartate | 1 in 11 | |
| Morphine valerate | 1 in 5 | |
| Morphine hydrobromide | 1 in 25 | |
| Morphine hydrochloride | 1 in 17.5 | |
| Propoxyphene hydrochloride | 1 in 0.3 | |
| Anticonvulsants | | |
| Phenobarbital sodium | 1 in 3 | 7.41 |
| Phenytoin sodium | soluble | 8.3 |
| Troxidone | 1 in 13 | |
| Ethosuximide | 1 in 4.5 | 9.0 |
| Valproate sodium | 1 in 5 | 4.8 |
| Tranquilizers | | |
| Acetophenazine maleate | 1 in 10 | |
| Chlorpromazine hydrochloride | 1 in 0.4 | 9.3 |
| Fluphenazine hydrochloride | 1 in 10 | 3.9, 8.1 |
| Prochlorperazine edisylate | 1 in 2 | 3.7, 8.1 |
| Promazine hydrochloride | 1 in 1 | 9.4 |
| Thioridazine hydrochloride | 1 in 9 | 9.5 |
| Trifluoroperazine hydrochloride | 1 in 2 | 8.1 |
| Lithium citrate | 1 in 2 | |
| Molindone hydrochloride | freely soluble | 6.9 |
| Thiothixine hydrochloride | 1 in 8 | |

-continued

| DRUG | SOLUBILITY (AQUEOUS) | pKA |
|---|---|---|
| Stimulants | | |
| Benzphetamine hydrochloride | freely soluble | 6.6 |
| Dextroamphetamine sulphate | 1 in 10 | 9.9 |
| Dextroamphetamine phosphate | 1 in 20 | 9.9 |
| Diethylpropion hydrochloride | freely soluble | |
| Fenfluramine hydrochloride | 1 in 20 | 9.1 |
| Methamphetamine hydrochloride | 1 in 2 | |
| Methylphenidate hydrochloride | freely soluble | 8.8 |
| Phendimetrazine tartrate | freely soluble | 7.6 |
| Phenmetrazine hydrochloride | 1 in 0.4 | 8.4 |
| Caffeine citrate | 1 in 4 | 14 |
| Barbiturates | | |
| Amylobarbitone sodium | 1 in 1 | 7.8 |
| Butabarbital sodium | freely soluble | 7.9 |
| Secobarbital sodium | 1 in 3 | 7.5 |
| Sedatives | | |
| Hydroxyzine hydrochloride | 1 in 1 | 2.6, 7.0 |
| Methyprylon | 1 in 14 | 12 |
| Expectorants | | |
| Potassium Iodide | 1 in 0.7 | |
| Antiemetics | | |
| Benzaquinamide hydrochloride | 1 in 10 | 5.9 |
| Metoclopramide HCl | 1 in 0.7 | 7.3, 9.0 |
| Trimethobenzamide hydrochloride | 1 in 2 | 8.3 |
| GI Drugs | | |
| Ranitidine hydrochloride | 1 in 2 | 8.2, 2.7 |
| Heavy Metal Antagonists | | |
| Penicillamine | 1 in 9 | 1.8 |
| Penicillamine HCl | 1 in 1 | 8.0, 10.8 |
| Antithyroid Agents | | |
| Methimazole | 1 in 5 | |
| Genitourinary Smooth Muscle Relaxants | | |
| Flavoxate hydrochloride | freely soluble | |
| Oxybutynin hydrochloride | freely soluble | 6.96 |
| Vitamins | | |
| Thiamine hydrochloride | 1 in 1 | 4.8, 9.0 |
| Ascorbic acid | 1 in 3 | 4.2, 11.6 |
| Unclassified Agents | | |
| Amantadine hydrochloride | 1 in 2.5 | 10.4 |
| Colchicine | 1 in 20 | 1.7, 12.4 |
| Etidronate disodium | freely soluble | |
| Leucovorin calcium | very soluble | 3.1, 4.81 10.4 |
| Methylene blue | 1 in 25 | −1 |
| Potassium chloride | 1 in 3 | |
| Pralidoxime chloride | 1 in 2 | 8 |

In the following description the active ingredient of high water solubility will be illustrated by reference to the opioid drug, morphine. However, this is illustrative only and the invention is in no way restricted thereto. Preferably, the active ingredient is an opiate selected from the group consisting of the salts of codeine, dextromoramide, hydrocodone, hydromorphine, pethidine, methadone, morphine and propoxyphene. More preferably, the active ingredient is an acid addition salt of one of these opiates such as morphine sulfate, morphine acetate, morphine lactate, morphine meconate, morphine nitrate, morphine phosphate, morphine phthalate, morphine tartate, morphine valerate, morphine hydrochloride, morphine hydrobromide, etc.

It will be understood that acid addition salts may be formed in the core particles of the pharmaceutical composition claimed herein by separate addition of opiate compound and an acid to the core formulation. Such indirectly obtained acid addition salts are within the scope of the present invention. Formulations obtained by other indirect methods, such as ion exchange, which result in suitable acid addition salts in the core formulation are also within the scope of the present invention.

Morphine acts as an agonist primarily at mu, kappa and perhaps delta receptors in the central nervous system. By acting on these receptors, morphine causes analgesia due to a receptor-mediated central action on pain perception, together with a receptor-mediated modulatory effect on the central transmission of noxious sensation. Morphine also causes drowsiness and euphoria (though sometimes dysphoria, particularly in those who are free of pain).

The pharmaceutical pellet composition according to the present invention may include a plurality of coated core elements.

The pharmaceutical composition may be provided in any suitable unit dosage form. An encapsulated form may be used.

The pharmaceutical pellet composition may be provided in a pellet or tableted pellet form. A tablet may be formed by compression of the pellets optionally with the addition of suitable excipients.

In a preferred aspect of the present invention the core coating, in use, generates a dissolution profile for the sustained release composition, which is equal to or greater than the minimum dissolution profile required to provide substantially equivalent bioavailability to a capsule, tablet or liquid containing an equal amount of the at last one active ingredient in an immediate release form.

"Dissolution profile" as used herein, means a plot of amount of active ingredient released as a function of time. The dissolution profile may be measured utilizing the Drug Release Test (724) which incorporates standard test USPXXII 1990. (Test(711)). A profile is characterized by the test conditions selected. Thus the dissolution profile may be generated at a preselected shaft speed, temperature and pH of the dissolution media.

A first dissolution profile may be measured at a pH level approximating that of the stomach. At least a second dissolution profile may be measured at pH levels approximating that of at least one point in the intestine.

A highly acidic pH may simulate the stomach and a less acidic to basic pH may simulate the intestine. By the term "highly acidic pH" as used herein we mean a pH in the range of approximately 1 to 4. By the term "less acidic to basic pH" we mean a pH of greater than 4 up to approximately 7.5, preferably approximately 6 to 7.5.

A pH of approximately 1.2 may be used to simulate the pH of the stomach.

A pH of approximately 6.0 to 7.5 preferably 7.5 may be used to simulate the pH of the intestine.

Accordingly in a further preferred aspect, a first dissolution profile is measured at a pH level approximating that of the stomach and a second dissolution profile is measured at a pH level approximating that of at least one point in the intestine; the first and second dissolution profiles for the sustained release composition each being equal to or greater than the minimum dissolution required to provide substantially equivalent bioavailability to a capsule, tablet or liquid containing the at least one active ingredient in an immediate release form.

More preferably, the composition, in use, exhibits less fluctuations in plasma concentrations in active ingredient at steady state over a 24 hour period, relative to the active ingredient in an uncoated form and/or exhibits less diurnal variation in plasma concentration of active ingredient relative to known capsules or tablets containing the at least one active ingredient in a sustained release form.

For example, dissolution profiles have been generated which exhibit bioavailability substantially equivalent to, or better than, commercially known morphine compositions including MS Contin, MST Continus and morphine solution.

Accordingly, in a preferred aspect of the present invention there is provided a sustained release pharmaceutical pellet composition including
a core element including a morphine compound; and a
core coating for the core element which is partially soluble at a highly acidic pH to provide a slow rate of release of morphine compound and wherein the morphine compound is available for absorption at a relatively constant faster rate in the intestine over an extended period of time.

It will be understood that further since the active ingredient is provided in a sustained release pellet form significantly less fluctuations in plasma concentrations of active ingredients at steady state over a 24 hour period are encountered, which may allow for less frequent dosing relative to the active ingredient in an uncoated form. This is expected to result in less toxic and more effective therapeutic activity.

Similarly, it has been found that the pharmaceutical pellet composition according to the present invention exhibits less diurnal variation in plasma concentrations of active ingredient than prior art preparations, for example when administered on a two, three or four times daily dosage regimen.

Moreover, the pharmaceutical pellet composition according to the present invention shows no evidence of dose dumping. The relative bioavailability of the active ingredient generated from the pharmaceutical pellet composition is not compromised by food so that compliance will improve as the product may be taken without regard to meals.

Moreover, since the core coating is partially soluble at an acidic pH, for example as encountered in the stomach of the patients, some slow release of active ingredient will occur in the stomach. The slow rate of release of active ingredient may also be at a relatively constant rate.

The active ingredient may be available for absorption even in regions of the gastrointestinal tract which are not sufficiently alkaline to dissolve the enteric core coating component.

Thus the active ingredient is available for absorption in an absorption region substantially immediately after the pyloric sphincter in the patient. Such an absorption region may generally be characterized by a pH between approximately 1.2 and 5.5. Absorption will occur in the small intestine. But, since absorption will continue over an extended period of time, additional absorption will occur some way into the large intestine.

Where the active ingredient of high solubility in water is a morphine compound, the morphine compound may take any suitable form. The morphine compound may be present in an anhydrous or hydrous form. The morphine compound may be provided in a salt form. Morphine sulphate is preferred. Morphine sulphate pentahydrate is particularly preferred.

Advantages of the sustained release pharmaceutical pellet composition according to the present invention may thus be summarized as follows (i) The time during which morphine blood levels at steady state are greater than or equivalent to 75% of the maximum blood level ($T \geq 0.75\ C_{max}$) may be 4 hours or greater, Generally $T \geq 0.75\ C_{max}$ may be approximately 6 hours or greater ($T \geq 0.75\ C_{max}$ for MS Contin has been reported to be 3.5. hours).

(ii) The time at which morphine blood levels reach their maximum concentration ($T_{max}$) may be between 4 and about 30 hours, generally between about 4 and about 12 hours.

(iii) The peak to trough variations in blood morphine concentrations at steady state will be between 60 and 100% (these variation for MS Contin have been reported to be approximately 300% and for Morphine Solution 4 hourly are approximately 200%).

(iv) Diurnal variations may be reduced.

(v) The co-administration of food will not significantly decrease the extent of morphine absorption. (The effect of food on morphine absorption from MS Contin is not known.)

(vi) Inter- and intra-subject variation in blood morphine pharmacokinectics may be reduced.

Accordingly, in a preferred aspect according to the present invention there is provided a sustained release pharmaceutical pellet composition including
a core element including at least one active ingredient of high solubility; and
a hybrid core coating which coating provides a slow rate of release of active ingredient at a highly acidic pH and a relatively constant faster rate of release at a less acidic to basic pH over an extended period of time.

Desirably, for some applications of the invention, the rate of release at the less acidic to basic pH is greater than the rate of release at the highly acidic pH, preferably 1.2 to three times greater.

The hybrid core coating may include at least one polymer which is substantially insoluble independent of pH (insoluble matrix polymer);
at least one enteric polymer which is substantially insoluble at acidic pH but at least partially soluble at a less acidic to basic pH (enteric polymer); and
at least one component which is at least partially soluble at acidic pH (acid soluble polymer).

It has been found necessary in order to achieve a slow rate of release at acidic pH for pH dependent or independent drugs, and faster relatively constant rate of release over an extended period of time to include the above three components in the hybrid core coating composition.

Preferably the enteric polymer is readily soluble at a less acidic to basic pH.

Preferably the at least partially soluble component is a readily water-soluble component.

Accordingly the hybrid core coating may include an effective amount of
a matrix (insoluble) polymer which is substantially insoluble independent of pH
an enteric polymer whose solubility is pH dependent, and
an at least partially acid soluble component.

The rate of dissolution at highly acidic pH of the hybrid core coating will depend on the amount of the at least one partially acid soluble component, the pH dependent and pH independent polymers, and the thickness of the coating. Typical core coatings may be in the range of approximately 5 to 200 um, preferably approximately 25 to 50 um. It will be understood, accordingly, that the rate of absorption may be modified by modifying the thickness and/or the composition of the hybrid core coating.

Once a minimum amount of the at least partially acid soluble component and/or the maximum thickness of the coating to achieve the minimum dissolution profile at an highly acidic pH has been established, then it is simply a matter of design choice to adjust the composition and/or thickness of coating as desired.

It has been found that the dissolution rate of the soluble drug at various pH's can be modified at will by altering the ratio of polymers. The ternary system of polymers according to the present invention allows greater flexibility than as known in prior art using only binary systems of polymers.

The at least one enteric polymer may be selected from cellulose acetate phthalate, hydroxypropyl methylcellulose phthalate (HPMCP), polyvinyl acetate phthalate, methacrylic acid copolymer, hydroxypropyl methylcellulose acetate succinate, shellac, cellulose acetate trimellitate and mixtures thereof. Particularly preferred enteric polymers include synthetic resin bearing carboxyl groups. The methacrylic acid: acrylic acid ethylester 1:1 copolymer sold under the trade designation "Eudragit L100-55" has been found to be suitable.

The at least one enteric polymer may be present in the coating in an amount of from approximately 1 to 60% by weight, preferably 2 to 20% by weight, more preferably 4 to 20% by weight, based on the total weight of the hybrid core coating excluding weight of filler and plasticiser.

The at least partially acid-soluble component may be selected from polymers such as polyvinyl pyrrolidone, hydroxypropyl cellulose, hydroxypropyl methylcellulose, polyethylene glycol having a molecular weight of from 1700 to 20,000, polyvinyl alcohol and monomers therefore such as sugars, salts, or organic acids and mixtures thereof.

The at least partially acid-soluble component may be present in the coating in amounts of from approximately 1 to 60%, preferably 15 to 40% by weight, more preferably 20 to 35% by weight, based on the total weight of the hybrid core coating excluding weight of filler and plasticiser.

The at least one insoluble matrix polymer may be any suitable pharmaceutically acceptable polymer substantially insoluble independent of pH. The polymer may be selected from ethylcellulose, acrylic and/or methacrylic ester polymers or mixtures thereof and the like may be used. Polymers or copolymers of acrylates or methacrylates having a low quaternary ammonium content may be used. The acrylic acid ethyl ester: methacrylic acid methyl ester (1:1) copolymer has been found to be suitable.

The at least one insoluble matrix polymer may be present in the coating in an amount of from approximately 1 to 85% by weight preferably 35 to 75% by weight, more preferably 45 to 65% by weight, based on the total weight of the hybrid core coating excluding weight of filler and plasticiser.

The hybrid core coating may further include at least one plasticiser; and optionally at least one filler.

Accordingly in a preferred aspect the hybrid core coating includes 0 to approximately 50% by weight, preferably 2.5 to 30% by weight, based on the total weight of the hybrid core coating of at least one plasticiser selected from diethyl phthalate, triethyl citrate, triethyl acetyl citrate, triacetin, tributyl citrate, polyethylene glycol and glycerol and the like; and 0 to approximately 75% by weight based on the total weight of the hybrid core coating of a filler selected from insoluble materials such as silicon dioxide, titanium dioxide, talc, alumina, starch, kaolin, polacrilin potassium, powdered cellulose, and microcrystalline cellulose and mixtures thereof.

The at least one plasticiser may be selected from diethyl phthalate, triethyl citrate, triethyl acetyl citrate, triacetin, tributyl citrate, polyethylene glycol having a molecular weight of from 200 to less than 1700 and glycerol and the like. It will be understood that the plasticiser used may be largely dictated by the polymer used in the coating formulation, and the compatibility of the plasticiser with coating solution or dispersion. It should be noted that acid or water soluble plasticisers can also be used to function as the partially acid soluble component. The plasticiser may function to improve the physical stability of the core coating. A plasticiser is particularly preferred where the polymer has a high glass transition temperature and/or is of a relatively low molecular weight.

The plasticiser may be present in any suitable effective amount. Amounts of from approximately 0 to 50% by weight preferably 2.5 to 30% by weight, more preferably 4 to 30% by weight, based on the total weight of the hybrid core coating, have been found to be suitable.

The filler may be present in any suitable effective amount. Amounts of from 0 to approximately 75% by weight, preferably 15 to 60% by weight, more preferably 25 to 45% by weight, based on the total weight of the hybrid core coating have been found to be suitable.

Accordingly in a further preferred aspect the hybrid core coating has a formulation

| | | |
|---|---|---|
| Ethylcellulose | 45 to 60% | |
| Methacrylic acid acrylic acid ethyl ester 1:1 copolymer | 5 to 20% | % excluding plasticiser and filler |
| Polyethylene glycol | 20 to 35% | |
| Diethyl phthalate | 2.5 to 30% | |
| Talc | 25 to 45% of total weight of hybrid core coating | |

In a preferred aspect of the present invention the core element of the pharmaceutical composition according to the present invention may include an effective amount of at least one active ingredient of high solubility; at least one core seed; and
at least one binding agent.

The active ingredient may be present in any suitable effective amount. The amount of active ingredient is dependent on the potency of the active ingredient and on the desired dosage strength and volume of a unit dose of the drug product. The active ingredient may be present in amounts of approximately 0.1 to 95% by weight, based on the total weight of the core element. The active ingredient may preferably be a morphine compound. The morphine compound may be present in amounts of approximately 10 to 60% by weight, based on the total weight of the core element.

The binding agent may be present in amounts of from approximately 0.1 to 45% by weight preferably approximately 0.1 to 20% by weight, more preferably approximately 3 to 15% by weight, based on the total weight of the core element.

The binding agent may be of any suitable type. Suitable binders may be selected from polyvinyl pyrrolidone, hydroxypropyl cellulose, hydroxypropyl methylcellulose, methylcellulose and hydroxyethyl cellulose, sugars and mixtures thereof. The binding agent may be provided in the form of a granulating solution. An aqueous or organic solvent may be included. Methanol, ethanol of mixtures thereof may be used as solvents.

The size and amount of the core seed may vary substantially from approximately 100 um to 1700 um depending upon the amount of active ingredient to be included. Accordingly, the core seeds may vary from approximately 5 to 99% by weight, preferably 40 to 90% by weight based on the total weight of the core element, depending on the potency of the active ingredient. The core seed may be of such a diameter to provide a final core element having a diameter of approximately 200 to 2000 um.

The core seed may be of any suitable type. A sugar or an active core seed may be used.

The core element may further include other carriers or excipients, fillers, stabilizing agents and colorants. Suitable fillers may be selected from insoluble materials such as silicon dioxide, talc, titanium dioxide, alumina, starch, kaolin, polacrilin potassium, powdered cellulose, and microcrystalline cellulose and mixtures thereof. Soluble fillers may be selected from mannitol, sucrose, lactose, dextrose, sodium chloride, sorbitol and mixtures thereof.

In a preferred aspect the core element includes an effective amount of at least one morphine compound; optionally
  at least one core seed; and
  at least one binding agent.

The core element may have a formulation

| | |
|---|---|
| Morphine sulphate | 10 to 60% by weight |
| Core seeds | 30 to 89.9% by weight |
| Hydroxypropylmethylcellulose | 0.1 to 10% by weight |

Alternatively the core element may have a formulation

| | |
|---|---|
| Morphine sulphate | 10 to 60% by weight |
| Core seeds | 30 to 87.5% by weight |
| Polyvinyl pyrrolidone | 2.5 to 10% by weight |

The hybrid core coating composition may be provided in the form of a solution, dispersion or suspension.

In the form of a solution, the solvent may be present in amounts of from approximately 25 to 97% by weight, preferably 85–97%, based on the total weight of the hybrid core coating composition. The solvent for the polymer may be a solvent such as water, methanol, ethanol, methylene chloride and mixtures thereof.

In the form of a dispersion or suspension, the diluting medium may be present in amounts of from approximately 25 to 97% by weight, preferably 75–97%, based on the total weight of the hybrid core coating composition and is comprised predominantly of water, preferably between about 80 to about 100% v/v of water.

Typical hybrid core coating formulations may be prepared in the amounts as follows:

| Core Coating Formulation | | |
|---|---|---|
| A. Insoluble matrix polymer | 45–65% | |
| Enteric polymer | 4–10% | % excluding |
| Acid soluble polymer | 15–35% | solvent and filler |
| Plasticiser | 4–30% | |
| Solvent | 85–97% of total coating formula | |
| B. Insoluble matrix polymer | 45–65% | |
| Enteric polymer | 4–20% | % excluding |
| Acid Soluble polymer | 15–35% | solvent and filler |
| Plasticiser | 4–30% | |
| Diluting medium | 75–97% of total coating formula | |

Optionally, an amount of filler not exceeding 50% of the core coating formulations weight excluding solvent, may be added.

In a further aspect of the present invention, there is provided a method for preparing a sustained release pharmaceutical pellet composition, which method includes providing
  a core element including
    at least one active ingredient of high solubility; and
    at least one binding agent; and
  a hybrid core coating composition including a solution, suspension or dispersion of
    at least one polymer which is substantially insoluble independent of pH;
    at least one enteric polymer which is substantially insoluble at acidic pH but at least partially soluble at a less acidic to basic pH; and
    at least one component which is at least partially soluble at acidic pH;
  introducing the core element into a fluidised bed reactor; and
  spraying the hybrid core coating composition onto the core element.

In a preferred aspect the method may further include the preliminary steps of providing
  at least one active ingredient of high solubility;
  at least one binding agent;
  at least one core seed; and
  coating the core seeds with the active ingredient and binding agent to form a core element.

In an alternative form the at least one binding agent is provided in a granulating solution. In this form the coating step may be conducted as a spheronisation process. The spheronisation process includes contacting the core seeds with the active ingredient and simultaneously adding the granulating solution thereto. The spheronisation process may be conducted in a spheronising machine.

In a further alternative aspect of the present invention, the method may further include the preliminary steps of providing
  at least one active ingredient of high solubility;
  at least one binding agent; and
  an effective amount of a solvent,
  mixing the ingredients; and
  subjecting the ingredients to an extrusion followed by marumerisation to form a core element.

The solvent may be an aqueous or organic solvent or mixtures thereof. The solvent may be present in an amount effective to allow the ingredients to be extruded.

The core elements formed are then subjected to a drying step. The drying step may be conducted in a fluidised bed or drying oven.

In a preferred form the at least one binding agent and active ingredient are provided in a solution or slurry. In this form the core seeds are sprayed with the solution or slurry. The spraying step may be conducted in any suitable coating equipment. The coating equipment may be a fluidised bed chamber, preferably a rotary fluid bed machine.

Spray coating of core elements may be undertaken utilizing bottom, top or tangentially located spray nozzles. A bottom spray nozzle may reside proximate to the base of the fluidised bed facing upwards while a top spraying nozzle is located above the contents of the bed and facing downwards. The spray nozzle may reside in the mid-section of the fluidised bed and be oriented such as to spray tangentially to the rotating core elements.

The sustained release pharmaceutical pellet composition may be administered under a similar dosage regimen to that used in the prior art. The multi-pellet encapsulated form may for example be administered every eight to twenty-four hours in sustained release form.

In a further preferred aspect of the present invention the pharmaceutical pellet composition incorporating morphine compound may provide effective pain relief with twice or three times or four times daily administration. Versatility of dosing may be achieved with 10 mg, 20 mg, 50 mg, 100 mg, 200 mg, 500 mg or any other dose strength of capsules required.

The pharmaceutical pellet composition may be in multipellet encapsulated, sprinkle sachet or tableted forms.

In accordance with a further aspect of the present invention, there is provided a method of treating pain associated conditions in patients requiring such treatment which method includes administering to a patient an effective amount of a sustained release pharmaceutical pellet composition including
- a core element including at least one morphine compound of high solubility; and
- a core coating for the core element which is partially soluble at a highly acidic pH and wherein the morphine compound is available for absorption at a relatively constant rate in the intestine over an extended period of time.

The method of treatment according to this aspect of the present invention is particularly applicable to the treatment of acute and chronic pain, particularly pain associated with terminal disease such as cancer and chronic backpain, as well as post-operative pain.

Preferably the pharmaceutical sustained release composition is provided in a unit dosage form and administration occurs at intervals of approximately 8 to 24 hours.

The present invention will now be more fully described with reference to the accompanying examples. It should be understood, however, that the following description is illustrative only and should not be taken in any way as a restriction on the generality of the invention specified above.

EXAMPLE 1

1. Formulation 1
   Core Composition

| | |
|---|---|
| Morphine Sulphate pentahydrate | 194 g |
| Core seeds | 170 g |
| Polyvinyl pyrrolidone | 37 g |
| Ethanol* | 185 g |
| Hybrid Core Coating Composition | |
| Polyethylene Glycol | 12 g |
| Ethylcellulose | 25 g |
| Diethyl phthalate | 2 g |
| Methacrylic acid:acrylic acid ethyl ester 1:1 copolymer | 5 g |
| Talc | 22 g |
| Ethanol* | 667 g |

2. Formulation 2
   Core Composition

| | |
|---|---|
| Morphine Sulphate pentahydrate | 194 g |
| Core Seeds | 170 g |
| Polyvinyl pyrrolidone | 37 g |
| Ethanol* | 185 g |
| Hybrid Core Coating Composition | |
| Polyethylene Glycol | 25 g |
| Ethylcellulose | 41 g |
| Diethyl phthalate | 3 g |
| Methacrylic acid:acrylic acid ethyl ester 1:1 copolymer | 4 g |
| Talc | 37 g |
| Ethanol* | 1106 g |

3. Formulation 3
   Core Composition

| | |
|---|---|
| Morphine Sulphate Pentahydrate | 264 g |
| Core Seeds | 722 g |
| Hydroxypropylmethylcellulose | 14 g |
| Ethanol* | 881 g |
| Water* | 105 g |
| Hybrid Core Coating Composition | |
| Polyethylene Glycol | 47 g |
| Ethylcellulose | 90 g |
| Diethyl phthalate | 19 g |
| Methacrylic acid:acrylic acid ethyl ester 1:1 copolymer | 20 g |
| Talc | 88 g |
| Ethanol* | 2509 g |

4. Formulation 4
   Core Composition

| | |
|---|---|
| Morphine Sulphate pentahydrate | 217.0 g |
| Core seeds | 771.6 g |
| Hydroxypropyl methylcellulose | 11.4 g |
| Water* | 86.1 g |
| Ethanol* | 723.9 g |
| Hybrid Core Coating | |
| Polyethylene glycol | 35.3 g |
| Ethycellulose | 100.6 g |
| Diethylphthalate | 19.4 g |
| Methacrylic acid:acrylic acid ethyl ester 1:1 copolymer | 21.2 g |
| Talc | 88.25 g |
| Ethanol* | 2508.0 g |

5. Formulation 5
   Core Composition

| | |
|---|---|
| Morphine Sulphate pentahydrate | 80.7 g |
| Core seeds | 1000.0 g |
| Hydroxypropylmethylcellulose | 8.9 g |
| Water* | 67.6 g |
| Ethanol* | 568.5 g |
| Hybrid Core Coating | |
| Polyethylene glycol | 14.6 g |
| Ethycellulose | 138.2 g |
| Diethylphthalate | 21.1 g |
| Methacrylic acid:acrylic acid ethyl ester 1:1 copolymer | 18.1 g |
| Talc | 96.0 g |
| Ethanol* | 2922.0 g |

6. Formulation 6
   Core Composition

| | |
|---|---|
| Morphine Sulphate pentahydrate | 80.7 g |
| Core seeds | 1000.0 g |
| Hydroxypropylmethylcellulose | 8.9 g |
| Water* | 67.6 g |
| Ethanol* | 568.5 g |
| Hybrid Core Coating | |

-continued

| | | |
|---|---|---|
| Polythylene glycol | 28.8 | g |
| Ethycellulose | 115.2 | g |
| Diethylphthalate | 21.1 | g |
| Methacrylic acid:acrylic acid ethyl ester 1:1 copolymer | 26.9 | g |
| Talc | 96.0 | g |
| Ethanol* | 2922.0 | g |

7. Formulation 7
Core Composition

| | | |
|---|---|---|
| Morphine Sulphate pentahydrate | 264 | g |
| Core seeds | 722 | g |
| Hydroxypropylmethylcellulose | 14 | g |
| Water* | 881 | g |
| Ethanol* | 105 | g |

Hybrid Core Coating

| | | |
|---|---|---|
| Polythylene glycol | 27.6 | g |
| Ethycellulose | 77.2 | g |
| Diethylphthalate | 15.9 | g |
| Methacrylic acid:acrylic acid ethyl ester 1:1 copolymer | 22.5 | g |
| Talc | 71.5 | g |
| Ethanol* | 2031.3 | g |

*Solvent is not present in final product.

Spheronised Core Manufacture (Core Composition 1 and 2)

The core seeds were placed in a spheroniser. The core seeds were then coated with a dry mixture of the active ingredients and inactive excipients whilst concomitantly adding a solution of the binder components. The wet cores so formed were then dried in a fluidised bed dryer for 1 hour.

Rotacoating Core Manufacture (Core Composition 3)

The core seeds were placed in a rotor fluid bed machine. The core seeds were then coated with a suspension or solution of the active ingredients and inactive excipients including at least one binding agent, in a suitable liquid. The wet cores so formed were then dried in a suitable drier for one hour.

Pellet Manufacture (a) The dried spheronised cores 1 and 2 were then placed in a fluid bed coating apparatus. The hybrid core coating compositions 1 and 2 were then sprayed onto the cores 1 and 2 to form Formulation 1 and 2 pellets respectively. At the conclusion of the process, the pellets were fluid bed dried.

(b) The dried cores 3 were then placed in a rotary fluid bed or conventional fluid bed coating apparatus. The hybrid core coating composition 3 was then sprayed onto the cores 3 to form Formulation 3 pellets.

A dissolution test was conducted on the pellet compositions 1, 2 and 3 utilizing the test method USPXXII 1990 (Test 711). A sample is dissolved in an aqueous medium previously degassed and equilibrated to 37° C. The media are USP pH 1.2 media without enzymes and pB 7.5 phosphate buffer. A sample of known volume is withdrawn at designated time intervals from the bath as directed and subjected to a suitable assay procedure. The mg of morphine sulphate as a function of time is plotted as the dissolution profile.

The tests were conducted at pH 1.2 and pH 7.5.

The baskets containing the samples were rotated at approximately 50 r.p.m. and the aqueous medium maintained at approximately 37° C.

Figure 2:
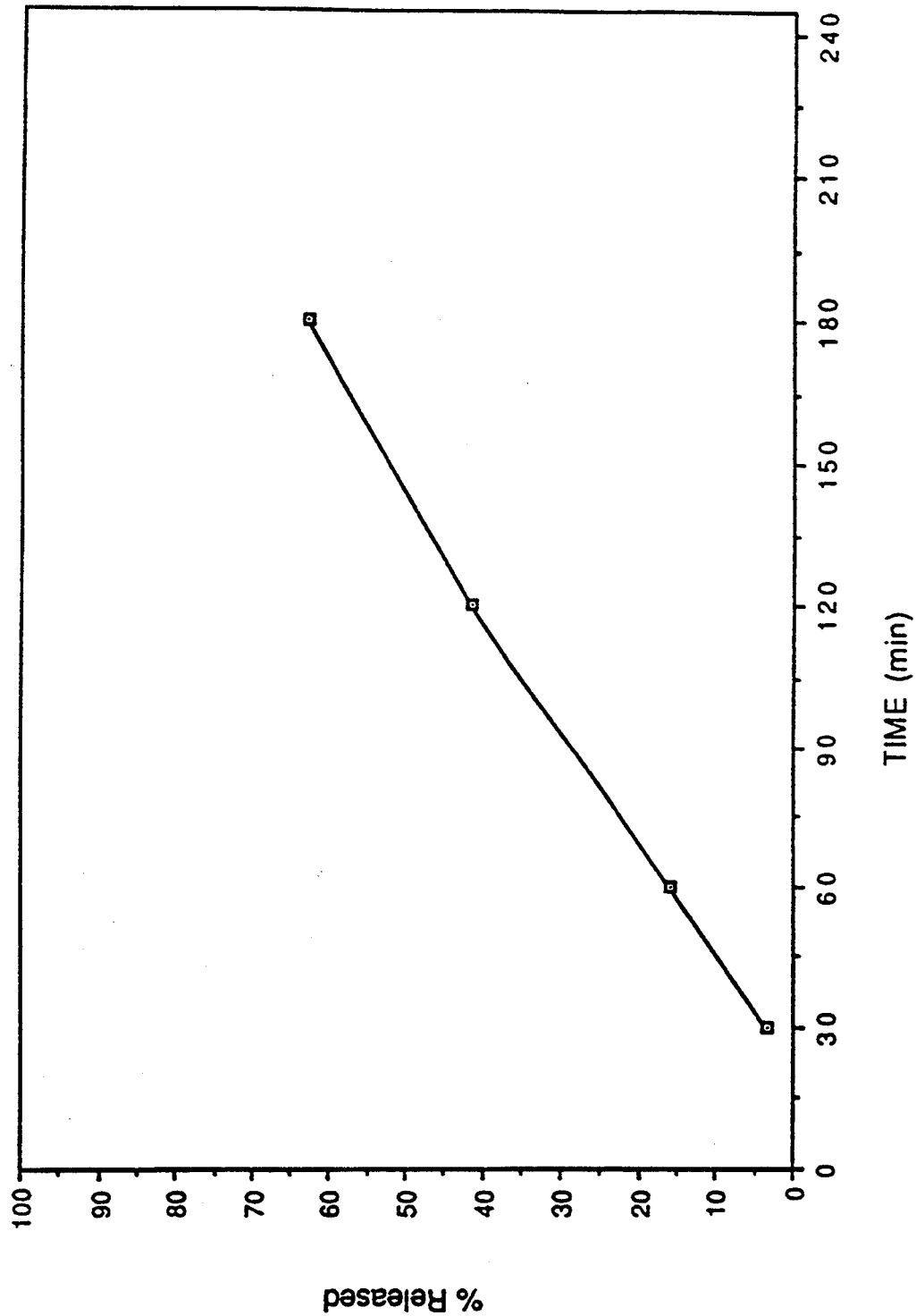
FIG. 2 shows the dissolution profile of morphine sulfate Formulation 1 at pH 7.5.
Figure 3:
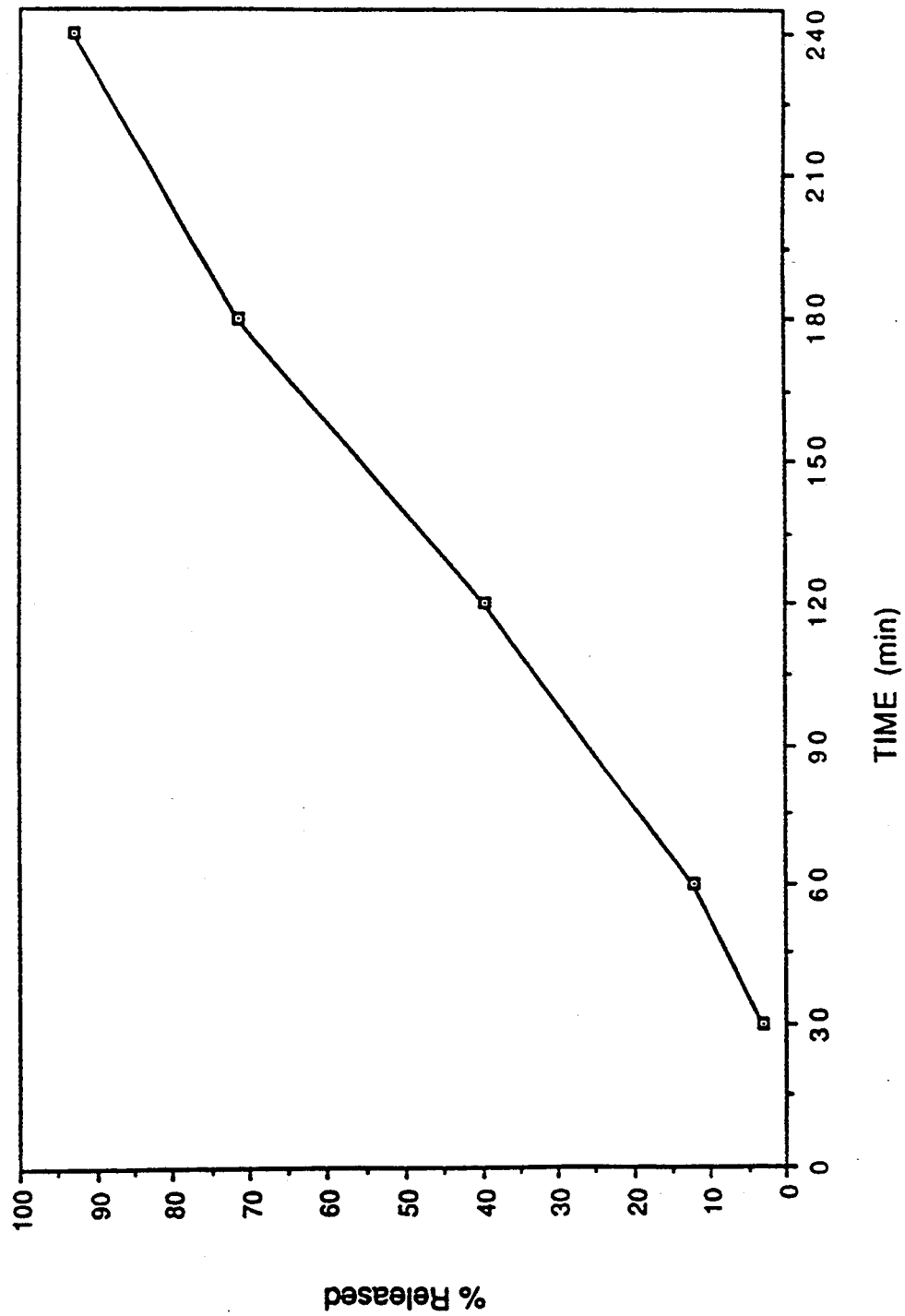
FIG. 3 shows the dissolution profile of morphine sulfate Formulation 2 at pH 1.2.
Figure 4:
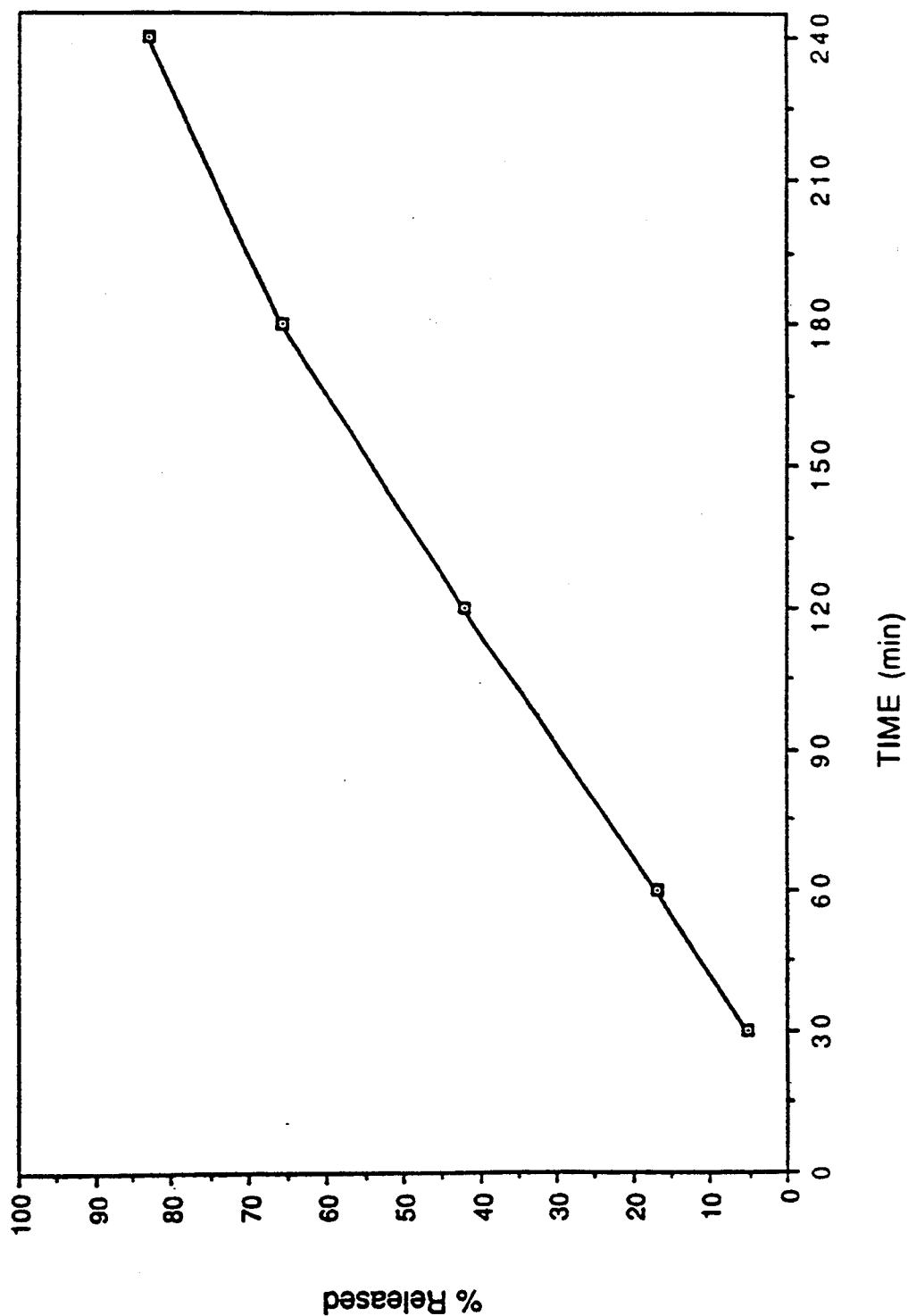
FIG. 4 shows the dissolution profile of morphine sulfate Formulation 2 at pH 7.5.
Figure 5:
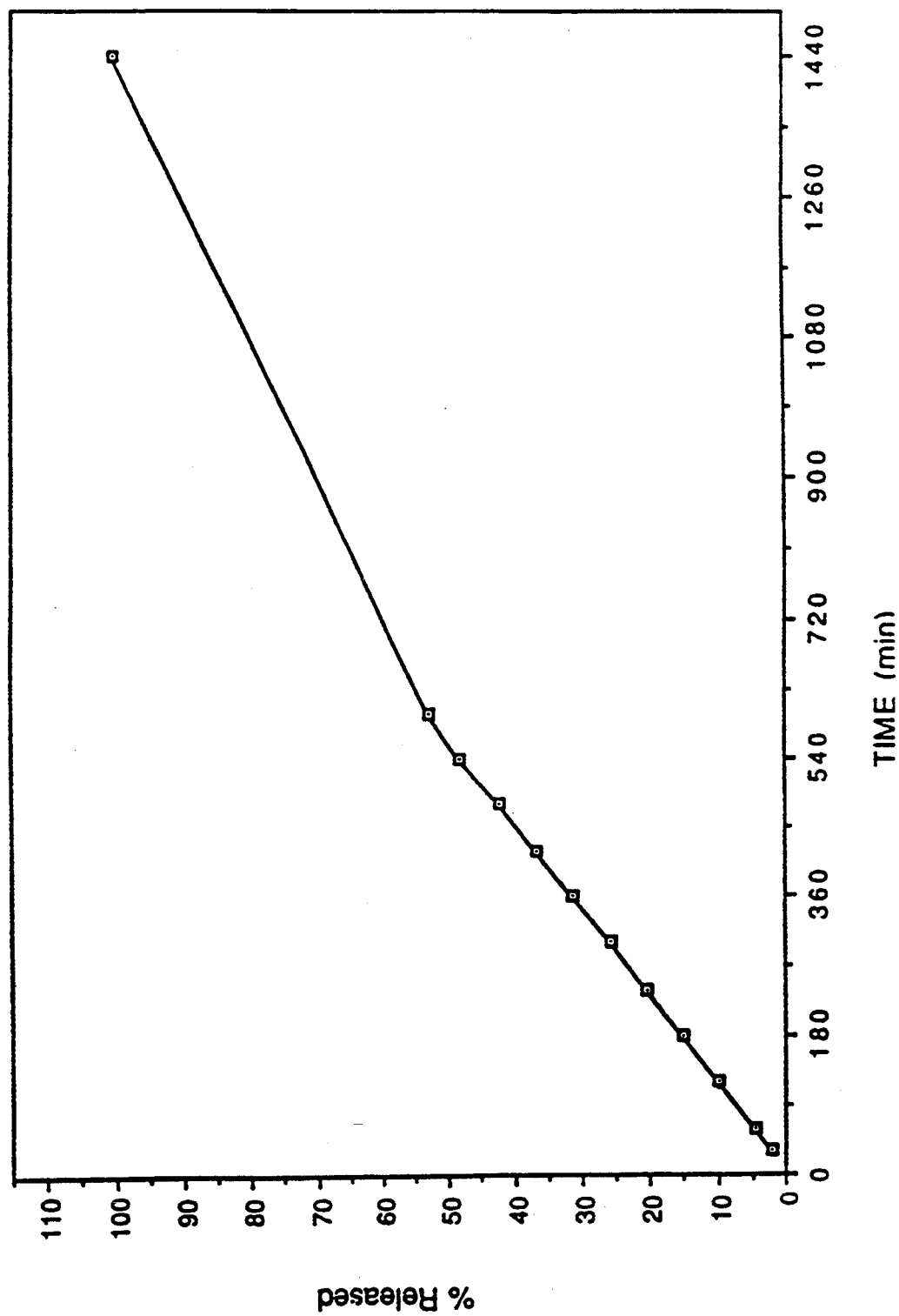
FIG. 5 shows the dissolution profile of Morphine sulfate Formulation 3 at pH 1.2.
Figure 6:
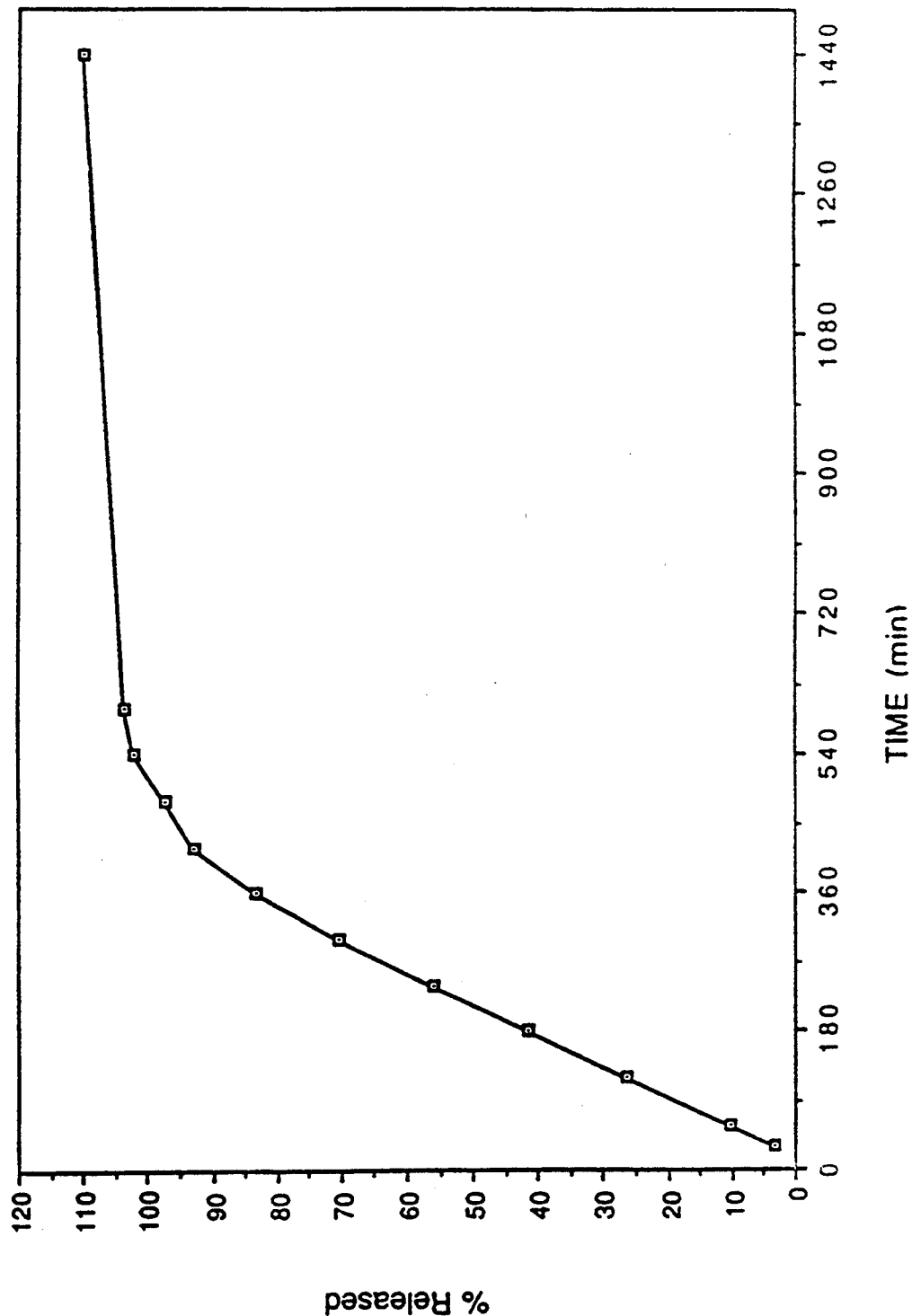
FIG. 6 shows the dissolution profile of morphine sulfate Formulation 3 at pH 7.5.

The results are given in Tables 1 to 6 and FIGS. 1 to 6 herein. The results for Formulation 1 at pH 1.2 and 7.5 are given in Tables 1 and 2 respectively. The hybrid coating on Formulation 1 pellet allows dissolution at pH 1.2, a significantly faster rate of dissolution is observed at pH 7.5. The results for Formulation 2 pellet at pH 1.2 and 7.5 are given in Tables 3 and 4 respectively, and are similar to those obtained from composition A.

The results for Formulation 3 pellets are similar to those achieved for Formulation 1 at pH 7.5. The overall results achieved for Formulation 3, however, illustrate a significant prolongation of release thereover. The dissolution results at 1.5 pH and 7.5 for formulation 3 are shown in Tables 5 and 6, respectively.

TABLE 1

DISSOLUTION DATA FOR FORMULATION 1 AT pH 1.2 (AVERAGED DATA FOR 3 SAMPLES)

| TIME MIN. | MG RELEASED | SD | % RELEASED | SD |
|---|---|---|---|---|
| 30 | 0.00 | 0.00 | 0.00 | 0.00 |
| 60 | 2.29 | 0.09 | 4.04 | 0.15 |
| 120 | 8.43 | 0.18 | 14.88 | 0.28 |
| 180 | 14.66 | 0.39 | 25.87 | 0.71 |

TABLE 2

DISSOLUTION DATA FOR FORMULATION 1 AT pH 7.5 (AVERAGED DATA FOR 3 SAMPLES)

| TIME MIN. | MG RELEASED | SD | % RELEASED | SD |
|---|---|---|---|---|
| 30 | 1.85 | 0.09 | 3.28 | 0.17 |
| 60 | 9.03 | 0.25 | 16.07 | 0.45 |
| 120 | 23.20 | 0.42 | 41.29 | 0.77 |
| 180 | 35.39 | 0.50 | 63.00 | 1.01 |

TABLE 3

DISSOLUTION DATA FOR FORMULATION 2 AT pH 1.2 (AVERAGED DATA FOR 3 SAMPLES)

| TIME MIN. | MG RELEASED | SD | % RELEASED | SD |
|---|---|---|---|---|
| 30 | 1.64 | 0.00 | 3.22 | 0.01 |
| 60 | 6.26 | 0.09 | 12.25 | 0.16 |
| 120 | 20.24 | 0.18 | 39.63 | 0.46 |
| 180 | 36.39 | 0.27 | 71.27 | 0.72 |
| 240 | 47.47 | 0.49 | 92.97 | 1.12 |

TABLE 4

DISSOLUTION DATA FOR FORMULATION 2 AT pH 7.5 (AVERAGED DATA FOR 3 SAMPLES)

| TIME MIN. | MG RELEASED | SD | % RELEASED | SD |
|---|---|---|---|---|
| 30 | 2.63 | 0.00 | 5.12 | 0.03 |
| 60 | 8.69 | 0.09 | 16.94 | 0.11 |
| 120 | 21.62 | 0.33 | 42.13 | 0.40 |
| 180 | 33.66 | 0.59 | 65.60 | 0.79 |
| 240 | 42.47 | 0.82 | 82.78 | 1.13 |

TABLE 5

DISSOLUTION DATA FOR FORMULATION 3 AT pH 1.2 (AVERAGED DATA FOR 3 SAMPLES)

| TIME MIN. | MG RELEASED | SD | % RELEASED | SD |
|---|---|---|---|---|
| 30 | 1.44 | 0.39 | 2.12 | 0.53 |
| 60 | 3.03 | 0.33 | 4.48 | 0.39 |
| 120 | 6.78 | 0.30 | 10.03 | 0.36 |
| 180 | 10.17 | 0.18 | 15.04 | 0.34 |
| 240 | 13.87 | 0.41 | 20.51 | 0.29 |
| 300 | 17.45 | 0.31 | 25.81 | 0.30 |
| 360 | 21.29 | 0.21 | 31.49 | 0.27 |
| 420 | 24.75 | 0.32 | 36.62 | 0.46 |
| 480 | 28.60 | 0.64 | 42.30 | 0.37 |
| 540 | 32.63 | 0.42 | 48.28 | 0.45 |
| 600 | 35.80 | 0.92 | 52.95 | 0.37 |
| 24 hours | 67.60 | 1.26 | 100.04 | 3.79 |

TABLE 6

DISSOLUTION DATA FOR FORMULATION 3
AT pH 7.5 (AVERAGED DATA FOR 3 SAMPLES)

| TIME MIN. | MG RELEASED | SD | % RELEASED | SD |
|---|---|---|---|---|
| 30 | 2.19 | 0.11 | 3.23 | 0.17 |
| 60 | 7.05 | 0.89 | 10.38 | 1.26 |
| 120 | 18.07 | 1.05 | 26.63 | 1.44 |
| 180 | 28.12 | 1.03 | 41.44 | 1.35 |
| 240 | 37.86 | 1.05 | 55.80 | 1.32 |
| 300 | 47.60 | 1.48 | 70.16 | 1.96 |
| 360 | 56.33 | 0.54 | 83.03 | 0.47 |
| 420 | 63.03 | 2.01 | 92.90 | 2.76 |
| 480 | 65.97 | 0.61 | 97.23 | 0.75 |
| 540 | 69.13 | 0.41 | 101.89 | 0.79 |
| 600 | 70.20 | 0.43 | 103.47 | 0.45 |
| 24 hours | 74.76 | 2.36 | 110.19 | 3.04 |

SD = Standard Deviation

Similar studies were conducted with formulations 4–6 and results similar to those obtained for formulation 3 were obtained. the $t_{\frac{1}{2}}$ for the dissolution at pH 1.2 ranged between about 8 and 10 hours, while the $t_{\frac{1}{2}}$ values at pH 7.5 ranged between about 3.5 and 4.5 hours.

The dissolution data for formulation 7 are shown in Tables 7 and 8. The data are similar to the data obtained for formulation 3.

TABLE 7

DISSOLUTION DATA FOR FORMULATION 7
AT pH 1.2 (AVERAGED DATA FOR 3 SAMPLES)

| TIME MIN. | MG RELEASED | SD | % RELEASED | SD |
|---|---|---|---|---|
| 30 | 0.68 | 0.39 | 1.22 | 0.71 |
| 60 | 1.53 | 0.10 | 2.74 | 0.17 |
| 120 | 5.29 | 0.28 | 9.44 | 0.59 |
| 180 | 8.15 | 0.11 | 14.54 | 0.30 |
| 240 | 11.12 | 0.18 | 19.84 | 0.36 |

TABLE 8

DISSOLUTION DATA FOR FORMULATION 7
AT pH 7.5 (AVERAGED DATA FOR 3 SAMPLES)

| TIME MIN. | MG RELEASED | SD | % RELEASED | SD |
|---|---|---|---|---|
| 30 | 1.12 | 0.00 | 2.01 | 0.00 |
| 60 | 4.52 | 0.28 | 8.15 | 0.52 |
| 120 | 14.48 | 0.68 | 26.08 | 1.29 |
| 180 | 24.28 | 0.73 | 43.74 | 1.41 |
| 240 | 33.88 | 0.68 | 61.03 | 1.36 |

EXAMPLE 2

Two sustained release morphine compositions in accordance with the present invention have been trialed in patients with back pain (fed and fasting) and in healthy volunteers (fasting). The results of these trials suggest that Faulding already has a product that is superior to a commercial product MS Contin with regard to sustained delivery of morphine. An investigation has also been initiated into understanding the effect that food has on the absorption of morphine.

The sustained release oral morphine compositions according to the present invention are designated Formulation 1 and Formulation 2.

1. PART A

A single dose 3 way crossover study under fasted conditions was conducted in six patients suffering chronic pain. On 3 occasions separated by one week, patients received a 50 mg oral morphine dose as either a solution (reference dose) or one of two sustained release formulations as pellets contained within a capsule (designated Formulation 1, a pH dependent release formulation; and Formulation 2, a pH independent release formulation). The doses were administered after an overnight fast. Venous blood samples were taken at specified time intervals from immediately after dose administration for 30 hours after the sustained release formulations and for 10 hours after the reference solution dose. The morphine concentration in the blood samples was quantitated using high pressure liquid chromatography (HPLC) with electrochemical detection. Table 9 summarizes the mean area under the curve (AUC); $C_{max}$ (maximum blood concentration); $T_{max}$ (time to reach peak blood concentration); $T_{\frac{1}{2}}$ (apparent terminal half life); $T \geq 0.75$ $C_{max}$ (time for which blood concentration was greater than 75% of $C_{max}$) and relative bioavailability (F %).

The results revealed that both Formulation 1 and Formulation 2 provide a sustained release relative to the reference solution as assessed by:

(1) a lower $C_{max}$ for the formulations;
(2) a longer $T_{max}$ for the formulations; and
(3) a longer time for which the blood morphine concentration was above 0.75 $C_{max}$ for the formulations.

There was a significant decrease in $C_{max}$ values for each formulation compared with the reference solution. The mean ($\pm$SD) $C_{max}$ for the solution was 73.6$\pm$30.9 ng/mL whereas the corresponding values for Formulation 1 and Formulation 2 were 21.6$\pm$7.1 ng/mL and 23.2$\pm$4.8 ng/mL respectively. The variability in $C_{max}$ for Formulations 1 and 2 as demonstrated by the coefficient of variation was significantly less than that of the solution in the same patients.

There was a significant increase in $T_{max}$ values for the formulations relative to that obtained with the reference solution. The mean ($\pm$SD) $T_{max}$ for solution was 1.07$\pm$1.09 hours whereas the equivalent values were 5.33$\pm$1.2 hours and 4.25$\pm$1.33 hours for Formulations 1 and 2 respectively. The variability in $T_{max}$ values for the formulations was less than that obtained for the solution in the same patients.

The time the blood morphine concentration was greater than or equal to 0.75 $C_{max}$ was significantly greater for the formulations compared to the reference solution dose. The mean time was 190 minutes for Formulation 1 and 237 minutes for Formulation 2 compared to only 59 minutes for the reference solution. Expressing these data as percentage of the time of the reference solution, Formulation 1 was 322% while Formulation 2 has 400% greater time that the blood morphine concentration was greater than 0.75 $C_{max}$ compared to the solution.

There was no significant difference between the AUC for the formulations and that obtained for the reference solution (Table 9).

The relative bioavailability for the formulations was calculated from the ratio of the AUC for the appropriate formulation relative to that obtained for the reference solution for each patient. The relative bioavailability was 83.5% for Formulation 1 and 102.6% for Formulation 2.

The AUC and relative bioavailability data suggest that the extent of absorption of morphine from the three different formulations is similar whereas the $C_{max}$, $T_{max}$ and $T \geq 0.75$ $C_{max}$ data indicate that the formulations exhibit the typical slower and prolonged absorption of a true sustained release preparation.

TABLE 9

RESULT OF STUDY PART A

| PARAMETER | SOLUTION MEAN | FORMULATION 1 | | FORMULATION 2 | |
|---|---|---|---|---|---|
| | | MEAN | OBSERVED DIFF | MEAN | OBSERVED DIFF |
| AUC (ng·h/mL) | 199.77 | 170.72 | −29.05 | 193.77 | −6.0 |
| SD | ±66.32 | ±86.3 | | ±46.35 | |
| CV % | 33 | 51 | | 24 | |
| $C_{max}$ (ng/mL) | 73.57 | 21.60 | −52.0 | 23.16 | −50.4 |
| SD | ±30.92 | ±7.12 | | ±4.76 | |
| CV % | 42 | 33 | | 21 | |
| $T_{max}$ (hours) | 1.07 | 5.33 | 4.26 | 4.25 | 3.18 |
| SD | ±1.1 | ±1.21 | | ±1.33 | |
| CV % | 103 | 23 | | 31 | |
| Bioavailability (F %) | 100.0 | 83.53 | −16.47 | 102.62 | 2.62 |
| SD | ±0.00 | ±27.87 | | ±25.77 | |
| CV % | 0 | 33 | | 25 | |
| $t_{\frac{1}{2}}$ (hours) | 3.02 | 6.58 | 3.56 | 7.65 | 4.63 |
| SD | ±1.97 | ±5.33 | | ±5.59 | |
| CV % | 65 | 81 | | 73 | |
| $T_{>0.75\ C_{max}}$ (minutes) | 59.0 | 189.8 | 130.8 | 237.3 | 178.3 |
| SD | ±37 | ±76 | | ±95 | |
| CV % | 63 | 40 | | 40 | |

2. PART B

A single dose 3 way crossover study under fed conditions was conducted in six patients suffering chronic pain. The same patients took part in both Parts A and B of this study. On 3 occasions separated by one week, patients received a 50 mg oral morphine dose as either a solution (reference dose) or one of two sustained release formulations as pellets contained within a capsule (designated Formulation 1, a pH dependent release formulation; and Formulation 2, a pH independent release formulation). The doses were administered after an overnight fast. Venous blood samples were taken at specified time intervals from immediately after dose administration for 30 hours after the sustained release formulations and for 10 hours after the reference solution dose. The morphine concentration in the blood samples was quantitated using high pressure liquid chromatography (HPLC) with electrochemical detection. Table 10 summarizes the mean area under the curve (AUC); $C_{max}$ (maximum blood concentration); $T_{max}$ (time to reach peak blood concentration); $T \geq 0.75\ C_{max}$ (time for which blood concentration was greater than 75% of $C_{max}$) and relative bioavailability (F %).

The results revealed that, in the presence of food, both Formulation 1 and 2 provide a sustained release relative to the reference solution as assessed by:

(1) a lower $C_{max}$ for the formulations;
(2) a longer $T_{max}$ for the formulations; and
(3) a longer time for which the blood morphine concentration was above 0.75 $C_{max}$ for the formulations.

There was a significant decrease in $C_{max}$ values for each formulation compared with the reference solution. The mean (±SD) $C_{max}$ for the solution was 80.7±26.4 ng/mL whereas the corresponding values for Formulation 1 and Formulation 2 formulations were 22.0±8.1 ng/mL and 32.6±18.1 ng/mL respectively. The variability in $C_{max}$ for formulations 1 and 2 as demonstrated by the coefficient of variation was similar for all formulations. The $C_{max}$ values for each formulation obtained under fed conditions were similar to the values obtained in the same patients under fasting conditions (Part A).

There was a significant increase in $T_{max}$ values for the formulations relative to that obtained with the reference solution. The mean (±SD) $T_{max}$ for solution was 1.32±1.65 hours whereas the equivalent values were 5.83±0.75 and 4.5±0.84 hours for Formulation 1 and 2 respectively. The variability in $T_{max}$ values for the formulations was less than that obtained for the solution. The $T_{max}$ values were similar under fed and fasted conditions for each respective formulation.

The time the blood morphine concentration was greater than or equal to 0.75 $C_{max}$ was significantly greater for the formulations compared to the reference solution dose. The mean time was 231.2 minutes for Formulation 1 and 168.5 minutes for Formulation 2 compared to only 52.2 minutes for the reference solution. Expressing these data as percentage of the time of the reference solution, Formulation 1 was 443% while Formulation 2 has 323% greater time that the blood morphine concentration was greater than 0.75 $C_{max}$ compared to the solution. The data for the time greater than 0.75 $C_{max}$ under fed and fasting conditions was similar for each respective formulation.

Under fed conditions, there was a significant difference between the AUC for the formulations and that obtained for the reference solution (Table 8) the reference solution having a greater AUC than either formulation. The mean areas were very similar for the formulations with mean values of 204.13±106.11 ng.h/mL and 225.09±138.52 ng.h/mL for Formulation 1 and Formulation 2 respectively. The mean AUC for the solution under fed conditions was 281.98±112.58 ng.h/mL. The intersubject variability in AUC was similar for all formulations as shown by the coefficient of variation.

A comparison of AUC data obtained under fed and fasted conditions shows that the AUC for the reference solution expressed as a ratio of fed/fasted was 1.41 (range 0.94 to 1.9) with all but one patient having a ratio of greater than unity. There was a similar trend with the Formulations in that the mean AUC obtained when the formulations were administered immediately after food were larger than the equivalent value obtained in the fasted state.

The primary concern was to establish that "dose dumping" did not occur with either formulation. The data indicate that the bioavailability of morphine from formulations in the presence of food is at least equivalent to and possibly greater than the bioavailability from the same formulation in the fasted state and that the formulations behave in a similar manner to the solution with regard to the influence of food on the absorption of morphine.

The relative bioavailability for the formulations relative to that obtained for the reference solution was 79.4% for Formulation 1 and 78.2% for Formulation 2.

The AUC and relative bioavailability data suggest that the extent of absorption of morphine from the formulations is similar but slightly less than the solution in the fed state whereas the $C_{max}$, $T_{max}$ and $T \geq 0.75$ $C_{max}$ data indicate that the formulations exhibit the typical slower and prolonged absorption of a true sustained release preparation.

TABLE 10

RESULT OF STUDY PART B

| PARAMETER | SOLUTION MEAN | FORMULATION 1 MEAN | FORMULATION 1 OBSERVED DIFF | FORMULATION 2 MEAN | FORMULATION 2 OBSERVED DIFF |
|---|---|---|---|---|---|
| AUC (ng · h/mL) | 281.98 | 204.13 | −77.85 | 225.09 | −56.89 |
| SD | ±112.58 | ±106.11 | | ±138.52 | |
| CV % | 40 | 52 | | 62 | |
| $C_{max}$ (ng/ml) | 80.66 | 22.00 | −58.66 | 32.63 | −48.03 |
| SD | ±26.44 | ±8.05 | | ±18.07 | |
| CV % | 33 | 37 | | 55 | |
| $T_{max}$ (hours) | 1.32 | 5.83 | 4.51 | 4.50 | 3.18 |
| SD | ±1.65 | ±0.75 | | ±0.84 | |
| CV % | 125 | 13 | | 19 | |
| Bioavailability (F %) | 100.0 | 79.4 | −20.6 | 78.2 | −21.8 |
| SD | ±0.00 | ±47.3 | | ±27.1 | |
| CV % | 0 | 60.0 | | 35.0 | |
| $T \geq 0.75$ $C_{max}$ (minutes) | 52.2 | 231.2 | 179.0 | 168.5 | 116.3 |
| SD | ±39.3 | ±73.9 | | ±55.5 | |
| CV % | 75 | 32 | | 33 | |

EXAMPLE 3

A single dose 2-way crossover study was conducted in eight adult patients suffering chronic pain associated with non-terminal disease states. All study doses were taken fasting and food was withheld for the first 12 hours of each study period. The mean data represent data from 8 patients taking reference solution and 9 patients taking Formulation 3 capsule.

On two occasions separated by one week, the volunteers received a 100 mg oral morphine dose administered as either three 33.3 mg doses in solution (200 mL given at 0,4 and 8 hours) or a single dose of a sustained release formulation as pellets contained in a capsule (Formulation 3, a pH dependent release formulation). The capsule dose was administered with 200 mL of water and a further 200 mL of fluid was taken at 4 and 8 hours post dose administration, to mirror the fluid intake of the morphine solution dose.

Venous blood samples were collected pre-dose and at specified time intervals for 18 hours after the first of the three oral solution doses and for 32 hours following administration of the sustained release formulation. The morphine concentration in the study blood samples was quantitated using high pressure liquid chromatography (HPLC) with electrochemical detection. Table 11 summarises the mean area under the concentration versus time curve (AUC) for zero to 18 hours; $C_{max}$ (maximum observed blood concentration); $T_{max}$ (time to reach maximum observed blood concentration); $T \geq 0.75$ $C_{max}$ (time for which maximum observed blood concentration was greater than or equal to 75% of $C_{max}$) and relative bioavailability (F %). The profile for morphine concentration in the blood vs. time is shown in FIG. 7 for both the solution administrations and the Formulation 3 administration.

The study results indicated that, under fasting conditions, administration of the test product Formulation 3 provided a sustained release relative to the reference solution as assessed by:

(1) lower $C_{max}$ values for Formulation 3;
(2) longer $T_{max}$ values for Formulation 3; and
(3) longer values for the parameter $T \geq 0.75$ $C_{max}$ for Formulation 3.

There was a significant decrease in the $C_{max}$ values for Formulation 3 compared with the reference solution with mean (+SD) values of (34.24+12.25) ng/mL and (157.72+59.76) ng/mL for Formulation 3 and solution, respectively. The $C_{max}$ value for the solution was taken as three times the $C_{max}$ value following the first of the three solution doses. The variability in $C_{max}$ for Formulation 3 and solution as demonstrated by the coefficient of variation was minimal for the two products.

There was a significant increase in the $T_{max}$ values for Formulation 3 relative to that obtained following each dose of solution. The mean (+SC) $T_{max}$ for solution was (0.63+0.23) hours and for Formulation 3 was (7.67+2.06) hours. The variability in $T_{max}$ values for Formulation 3 was less than that obtained for the solution (27% vs 37%), respectively.

The mean time for which the maximum observed blood concentration was greater than or equal to 0.75 $C_{max}$ was 6.25 hours for Formulation 3 suggesting that the product possesses adequate sustained release properties.

There was not significant difference between the AUC (zero to 18 hours) values of the reference solution and Formulation 3. (Table 11).

The relative bioavailability for Formulation 3 compared to the reference solution was (102.06%) indicating that the extent of absorption of morphine for Formulation 3 is adequate.

The $T_{max}$ and $T \geq 0.75\ C_{max}$ values obtained following dosing with Formulation 3 suggest that, under fasting conditions, Formulation 3 possesses improved sustained release properties compared with those of the first prototypes Formulation 1 and Formulation 2. The concentration versus time profile of the mean data for Formulation 3 also substantiates this claim.

TABLE 11

| PARAMETER | SOLUTION MEAN (n = 8) | FORMULATION 3 MEAN (n = 9) | OBSERVED DIFFERENCE |
|---|---|---|---|
| AUC (0–18 h) (ng · h/mL) | 374.21 | 361.03 | −13.18 |
| SD | 155.52 | 131.94 | |
| CV % | 42 | 37 | |
| $C_{max}$ (ng/mL) | 157.72 | 34.24 | −123.48 |
| SD | 59.76 | 12.25 | |
| CV % | 38 | 36 | |
| $T_{max}$ (h) | 0.63 | 7.67 | 7.04 |
| SD | 0.23 | 2.06 | |
| CV % | 37 | 27 | |
| Bioavailability (F %) | 100.00 | 102.06 | 2.06 |
| SD | 00.00 | 18.47 | |
| CV % | 0 | 18 | |
| $t_{\frac{1}{2}}$ (h) | 3.48 | 5.77 | 2.29 |
| SD | 2.20 | 3.70 | |
| CV % | 63 | 64 | |
| $T \geq 0.75\ C_{max}$ (h) | NA | 6.25 | NA |
| SD | | 1.28 | |
| CV % | | 20 | |

NA = not applicable

Finally, it is to be understood that various other modifications and/or alterations may be made without departing from the spirit of the present invention as outlined herein.

What is claimed is:

1. A sustained release pharmaceutical pellet composition for administration to a patient at a predetermined dosage and interval which comprises: a core element containing a therapeutically effective amount of at least one active ingredient having an aqueous solubility of at least 1 in 30 and a coating on said core element which comprises the following components:
   (a) from 1 to 85% by weight of a matrix polymer which is insoluble at a pH of from 1 to 7.5 and contributes to the control of the rate of release of the active ingredient in the stomach and intestines;
   (b) from 1 to 30% of an enteric polymer which is substantially insoluble at a pH of from 1 to 4, sufficient to delay the release of the active ingredient in the stomach, but which is soluble at a pH of from 6 to 7.5 so as not to substantially delay release in the intestines;
   (c) from 1 to 60% of a compound soluble at a pH of from 1 to 4, sufficient to enable initiation of release of the active ingredient in the stomach; said percentages being by weight based on the total weight of components (a), (b), and (c); the ratio of the components (a), (b), and (c) in said coating being such that a dose of the pellet composition delivers to the patient a therapeutically effective amount of said active ingredient over the course of said predetermined interval, so as to maintain an active ingredient blood level at steady state of at least 75% of maximum blood level for more than approximately 4 hours and so that the time at which the active ingredient reaches its maximum concentration is between about 4 and about 30 hours.

2. The sustained release pharmaceutical pellet composition of claim 1 wherein the time at which the active ingredient reaches its maximum concentration is between about 4 and about 12 hours.

3. The sustained release pharmaceutical pellet composition of claim 1 wherein the active ingredient of high solubility is selected from the group consisting of antihistamines, antibiotics, antituberculosis agents, cholinergic agents, antimuscarinics, sympathomimetics, sympatholytic agents, autonomic drugs, iron preparations, haemostatics, cardiac drugs, antihypertensive agents, vasodilators, non-steroidal antiinflammatory agents, opiate agonists, anticonvulsants, tranquilizers, stimulants, barbiturates, sedatives, expectorants, antiemetics, gastrointestinal drugs, heavy metal antagonists, antithyroid agents, genitourinary smooth muscle relaxants and vitamins.

4. The sustained release pharmaceutical pellet composition of claim 3 wherein the active ingredient is an opiate agonist selected from the group consisting of the salts of codeine, dextromoramide, hydrocodone, hydromorphine, pethidine, methadone, morphine and propoxyphene.

5. The sustained release pharmaceutical pellet composition of claim 1 wherein the active ingredient has a first dissolution profile measured at a pH of from 1 to 4, and a second dissolution profile measured at a pH of about 7.5 and wherein said first and second dissolution profile are each at least equal to the minimum dissolution required to provide substantially the same bioavailability as with an immediate release oral dosage form.

6. The sustained release pharmaceutical pellet composition of claim 5 wherein the composition, in use, minimizes fluctuations in the plasma concentration of the active ingredient in said patient.

7. The sustained release pharmaceutical pellet composition of claim 1 wherein the coating contains:
   as component (a), ethyl cellulose, a quaternary ammonium acrylic or methacrylic polymer, an acrylic or a methacrylic ester copolymer or a mixture thereof;
   as component (b), cellulose acetate phthalate, hydroxypropyl methylcellulose phthalate, polyvinyl acetate phthalate, methacrylic acid:acrylic acid ester copolymer, hydroxypropyl methylcellulose acetate succinate, shellac, cellulose acetate trimellitate and mixtures thereof; and
   as component (c), polyvinylpyrrolidone, hydroxypropyl cellulose, hydroxypropyl methylcellulose, polyethylene glycol having a molecular weight of from 1700 to 20,000, polyvinyl alcohol and monomers therefor and mixtures thereof.

8. The sustained release pharmaceutical pellet composition of claim 7 wherein the coating comprises:
   35 to 75% by weight of component (a);
   2–20% by weight of component (b); and
   15–40% by weight of component (c).

9. The sustained release pharmaceutical pellet composition of claim 7 wherein the coating also includes up to 50% of plasticizer selected from diethyl phthalate, triethyl citrate, triethyl acetyl citrate, triethyl acetin, tributyl citrate, polyethylene glycol having a molecular weight of from 200 to less than 1700 or glycerol and up to 75% of a filler selected from silicon dioxide, titanium dioxide, talc, alumina, starch, kaolin, polacrilin potassium, powdered cellulose and microcrystalline cellulose and mixtures thereof, said percentages being based on the total weight of the coating.

10. The sustained release pharmaceutical pellet composition of claim 9 wherein the coating contains:
component (a) 35 to 70%
component (b) 4 to 20%
component (c) 15 to 35%
plasticizer 4 to 30%.

11. A sustained release pharmaceutical pellet composition for administration to a patient at a predetermined dosage and interval which comprises: a core element containing as the active ingredient a therapeutically effective amount of an acid addition salt of morphine and a coating on said core element which comprises the following components:
(a) from 1% to 85% by weight of a matrix polymer which is insoluble at a pH of from 1 to 7.5 and contributes to the control of the rate of release of the active ingredient in the stomach and intestines;
(b) from 1 to 30% of an enteric polymer which is substantially insoluble at a pH of from 1 to 4, sufficient to delay the release of the active ingredient in the stomach, but which is soluble at a pH of from 6 to 7.5 so as not to substantially delay release in the intestines;
(c) from 1 to 60% of a compound soluble at a pH of from 1 to 4, sufficient to enable initiation of release of the active ingredient in the stomach;
said percentages being by weight based on the total weight of components (a), (b), and (c); the ratio of the components (a), (b), and (c) in said coating being such that a dose of the pellet composition delivers to the patient a therapeutically effective amount of said active ingredient over the course of said predetermined interval, so as to maintain an active ingredient blood level at steady state of at least 75% of maximum blood level for more than approximately 4 hours and so that the time at which the active ingredient reaches its maximum concentration is between about 4 and about 30 hours.

12. The sustained release pharmaceutical pellet composition of claim 11 wherein the time at which the active ingredient reaches its maximum concentration is between about 4 and about 12 hours.

13. The sustained release pharmaceutical pellet composition of claim 11 wherein said acid addition salt of morphine is morphine sulphate.

14. The sustained release pharmaceutical pellet composition of claim 11 wherein the composition, in use, minimizes fluctuations in the morphine compound concentration in the plasma of said patient.

15. The sustained release pharmaceutical pellet composition of claim 11 wherein the coating contains:
as component (a), ethyl cellulose, a quaternary ammonium acrylic or methacrylic polymer, an acrylic or a methacrylic ester copolymer or a mixture thereof;
as component (b), cellulose acetate phthalate, hydroxypropyl methylcellulose phthalate, polyvinyl acetate phthalate, methacrylic acid ester copolymer, hydroxypropyl methylcellulose acetate succinate, shellac, cellulose acetate trimellitate and mixtures thereof; and
as component (c), polyvinylpyrrolidone, hydroxypropyl cellulose, hydroxypropyl methylcellulose, polyethylene glycol having a molecular weight of from 1700 to 20,000, polyvinyl alcohol and monomers therefore and mixtures thereof.

16. The sustained release pharmaceutical pellet composition of claim 15 wherein the coating comprises:
35 to 75% by weight of component (a);
2-20% by weight of component (b); and
15-40% by weight of component (c).

17. The sustained release pharmaceutical pellet composition of claim 15 wherein the coating comprises:
polyethylene glycol having a molecular weight of from 1700 to 20,000 15 to 40%
ethylcellulose 45 to 65%
methacrylic acid: acrylic
acid ethylester 1:1 copolymer 4 to 20%.

18. A sustained release pharmaceutical pellet composition for administration to a patient at a predetermined dosage and interval which comprises: a core element containing a therapeutically effective amount of at least one active ingredient having an aqueous solubility of at least 1 in 30 and a coating on said core element which comprises the following components:
(a) at least 35% by weight of a matrix polymer which is insoluble at a pH of from 1 to 7.5 and is composed of ethyl cellulose, a quaternary ammonium acrylic or methacrylic polymer, an acrylic or a methacrylic ester copolymer or a mixture thereof which contributes to the control of the release of the active ingredient in the stomach and intestines;
(b) from 1 to 30% of an enteric polymer which is substantially insoluble at a pH of from 1 to 4, sufficient to delay the release of the active ingredient in the stomach, but which is soluble at a pH of from 6 to 7.5 so as not to substantially delay release in the intestines;
(c) from 1 to 60% of a compound soluble at a pH of from 1 to 4, sufficient to enable initiation of release of the active ingredient in the stomach; said percentages being by weight based on the total weight of components (a), (b), and (c); the ratio of the components (a), (b), and (c) in said coating being such that a dose of the pellet composition delivers to the patient a therapeutically effective amount of said active ingredient over the course of said predetermined interval, so as to maintain an active ingredient blood level at steady state of at least 75% of maximum blood level for more than approximately 4 hours and so that the time at which the active ingredient reaches its maximum concentration is between about 4 and about 30 hours.

19. The sustained release pharmaceutical pellet composition of claim 18 wherein the time at which the active ingredient reaches its maximum concentration is between about 4 and about 12 hours.

20. A sustained release pharmaceutical pellet composition for administration to a patient at a predetermined dosage and interval which comprises: a core element containing as the active ingredient a therapeutically effective amount of an acid addition salt of morphine and a coating on said core element which comprises the following components:
(a) at least 35% by weight of a matrix polymer which is insoluble at a pH of from 1 to 7.5 and is composed of ethyl cellulose, a quaternary ammonium acrylic or methacrylic polymer, an acrylic or a methacrylic ester copolymer or a mixture thereof which contributes to the control of the release of the active ingredient in the stomach and intestines;
(b) from 1 to 30% of an enteric polymer which is substantially insoluble at a pH of from 1 to 4, sufficient to delay the release of the active ingredient in the stomach, but which is soluble at a pH of from 6 to 7.5 so as not to substantially delay release in the intestines;
(c) from 1 to 60% of a compound soluble at a pH of from 1 to 4, sufficient to enable initiation of release of the active ingredient in the stomach; said percentages being by weight based on the total weight of components (a), (b), and (c); the ratio of the components (a), (b), and (c) in said coating being such that a dose of the pellet composition delivers to the patient a therapeutically effective amount of said active ingredient over the course of said predetermined interval, so as to maintain an active ingredient blood level at steady state of at least 75% of maximum blood level for more than approximately 4 hours and so that the time at which the active ingredient reaches its maximum concentration is between about 4 and about 30 hours.

21. The sustained release pharmaceutical pellet composition of claim 20 wherein the time at which the active ingredient reaches its maximum concentration is between about 4 and about 12 hours.

* * * * *

UNITED STATES PATENT AND TRADEMARK OFFICE
CERTIFICATE OF CORRECTION

PATENT NO. : 5,378,474  
APPLICATION NO. : 08/021276  
DATED : January 3, 1995  
INVENTOR(S) : Angelo M. Morella It is certified that error appears in the above-identified patent and that said Letters Patent is hereby corrected as shown below:

Col. 24 lines 14-26, should read,

3. The sustained release pharmaceutical pellet composition of claim 1 wherein the active ingredient is selected from the group consisting of antihistamines, antibiotics, antituberculosis agents, cholinergic agents, antimuscarinics, sympathomimetics, sympatholytic agents, autonomic drugs, iron preparations, haemostatics, cardiac drugs, antihypertensive agents, vasodilators, non-steroidal antiinflammatory agents, opiate agonists, anticonvulsants, tranquilizers, stimulants, barbiturates, sedatives, expectorants, antiemetics, gastrointestinal drugs, heavy metal antagonists, antithyroid agents, genitourinary smooth muscle relaxants and vitamins.

Col. 24 lines 46-61, should read,

7. The sustained release pharmaceutical pellet composition of claim 1 wherein the coating contains:
   as component (a), ethyl cellulose, a quatemary ammonium acrylic or methacrylic polymer, an acrylic or a methacrylic ester copolymer or a mixture thereof;
   as component (b), cellulose acetate phthalate, hydroxypropyl methylcellulose phthalate, polyvinyl acetate phthalate, methacrylic acid:acrylic acid ester copolymer, hydroxypropyl methylcellulose acetate succinate, shellac, cellulose acetate trimellitate or mixtures thereof; and
   as component (c), polyvinylpyrrolidone, hydroxypropyl cellulose, hydroxypropyl methylcellulose, polyethylene glycol having a molecular weight of from 1700 to 20,000, polyvinyl alcohol and monomers therefor or mixtures thereof.

UNITED STATES PATENT AND TRADEMARK OFFICE
CERTIFICATE OF CORRECTION

PATENT NO. : 5,378,474
APPLICATION NO. : 08/021276
DATED : January 3, 1995
INVENTOR(S) : Angelo M. Morella It is certified that error appears in the above-identified patent and that said Letters Patent is hereby corrected as shown below:

Col. 25 lines 60-67, should read,

15. The sustained release pharmaceutical pellet composition of claim 11 wherein the coating contains:
    as component (a), ethyl cellulose, a quaternary ammonium acrylic or methacrylic polymer, an acrylic or a methacrylic ester copolymer or a mixture thereof;
    as component (b), cellulose acetate phthalate, hydroxypropyl methylcellulose phthalate, polyvinyl acetate phthalate, methacrylic acid ester copolymer, hydroxypropyl methylcellulose acetate succinate, shellac cellulose acetate trimellitate or mixtures thereof; and
    as component (c), polyvinylpyrrolidone, hydroxypropyl cellulose, hydroxypropyl methylcellulose, polyethylene glycol having a molecular weight of from 1700 to 20,000, polyvinyl alcohol and monomers therefore or mixtures thereof.

Signed and Sealed this

Tenth Day of April, 2007

JON W. DUDAS
*Director of the United States Patent and Trademark Office*